(12) United States Patent
Miller

(10) Patent No.: US 8,110,794 B2
(45) Date of Patent: Feb. 7, 2012

(54) SOFT ABLATIVE DESORPTION METHOD AND SYSTEM

(76) Inventor: R. J. Dwayne Miller, Port Credit (CA)

(*) Notice: Subject to any disclaimer, the term of this patent is extended or adjusted under 35 U.S.C. 154(b) by 171 days.

(21) Appl. No.: 12/656,536

(22) Filed: Feb. 2, 2010

(65) Prior Publication Data
US 2010/0213367 A1 Aug. 26, 2010

Related U.S. Application Data

(60) Provisional application No. 61/202,161, filed on Feb. 2, 2009.

(51) Int. Cl.
*H01J 49/04* (2006.01)
*H01J 49/16* (2006.01)
*G01N 1/28* (2006.01)

(52) U.S. Cl. ........ 250/282; 250/281; 250/288; 250/425; 250/492.1; 250/492.2; 219/121.6; 436/174

(58) Field of Classification Search .................. 250/282, 250/281, 288, 425, 492.1, 492.2; 219/121.6; 436/174
See application file for complete search history.

(56) References Cited

U.S. PATENT DOCUMENTS

| | | |
|---|---|---|
| 6,156,030 A | 12/2000 | Neev |
| 6,414,320 B1 | 7/2002 | Ishikawa et al. |
| 7,852,886 B2 * | 12/2010 | Miller et al. ............ 372/21 |
| 2003/0090792 A1 | 5/2003 | Kenny et al. |
| 2006/0195072 A1 * | 8/2006 | Miller ............ 606/2 |

FOREIGN PATENT DOCUMENTS
WO 2004/108878 12/2004

OTHER PUBLICATIONS

Syage and Evans, "Photoionization Mass Spectrometry: A Powerful New Tool for Drug Discovery", Spectroscopy, Nov. 2001, vol. 16(11), http://spectroscopyonline.findanalytichem.com/spectroscopy/data/articlestandard/spectroscopy/452001/1111/article.pdf.

* cited by examiner

*Primary Examiner* — Nikita Wells
(74) *Attorney, Agent, or Firm* — Lynn C. Schumacher; Hill & Schumacher

(57) ABSTRACT

Methods and systems are provided for the soft desorption of analyte from a sample, in which an optical beam absorbed within an irradiate zone of the sample causes vibrational excitations of a component within the sample. The optical beam, providing sufficient energy to superheat the component, is provided for a time interval that is less than the time duration required for the loss of energy out of the irradiated zone due to thermal diffusion and acoustic expansion. The superheated component thus drives ablation within the irradiated zone, resulting in the soft desorption of analyte without ionization and fragmentation. The ejected ablation plume may be directed towards the inlet of a mass analysis device for detection of the desorbed analyte, which is preferably ionized by a linear resonant photo-ionization step.

80 Claims, 17 Drawing Sheets

SOFT ABLATIVE DESORPTION METHOD AND SYSTEM

CROSS-REFERENCE TO RELATED APPLICATION

This application claims priority to U.S. Provisional Application No. 61/202,161, filed on Feb. 2, 2009, and titled "Enhanced Molecular Detection Using Mass Spectroscopy with Time and Wavelength Multiplexed Laser Pulses", the entire contents of which are incorporated herein by reference.

FIELD OF THE INVENTION

The present invention relates to the desorption of analyte from a sample for analytical methods. More particularly, the present invention relates to methods of sample preparation for mass spectrometry.

BACKGROUND OF THE INVENTION

One of the most important problems in healthcare today is the early detection of disease states, whether one is trying to detect the onset of cancer or a specific viral infection. Most current assay technologies involve microliters or milliliters of sample and have moderate detection limits that require a significant analyte concentration. On the other hand, a single drop of blood or saliva may contain a complete chemical signature of particular states of wellness or disease-based on proteins or other molecules that are expressed during the state of distress are expressed in trace amounts. To detect trace analyte levels with such small sample volumes, a detection limit in the single-molecule range is required.

With the latest advances in mass spectrometry that provide high ionization efficiency and efficient ion collection optics, the state of the art is one step closer to achieving robust assays with low detection limits. However, in order to deliver quantitative assays with low detection limits in the single-molecule regime, two problems need to be solved.

The first problem associated with current mass spectrometry methods is that the process of ionization is not completely reproducible. Ionization is a necessary step that occurs after volatilization of the molecules of interest, but prior to the detection process based on the mass to charge ratio. Due to nonlinear fluctuations in the ionization yield from sample to sample, noise is introduced in the detection process that results in an elevated limit of detection. As a result, current methods, despite their high sensitivity, are not considered sufficiently quantitative for clinical diagnostics.

The two most common methods of introducing molecules to the gas phase are matrix-assisted laser desorption (MALDI) and electrospray. The very act of ionization is highly nonlinear for both methods of ionization. In the case of MALDI, there are complex chemical reactions involving proton exchange that are inherently nonlinear and occur under nonequilibrium conditions. Similarly, electrospray involves the charging of droplets that leads to statistical fluctuations that are amplified by the ensuing coulomb explosion process that strips off solvent molecules in the electrospray method. The number of ions generated for a given amount of material introduced to the gas phase by either method is irreproducible due to the highly nonlinear nature of the ion generation step. Small differences in conditions translate to large variations in the detected species.

To achieve a quantitative clinical diagnostic assay with a low coefficient of variation and a low limit of detection, it is essential for any measurement to be highly reproducible. To date, the nonlinear ionization process has prevented mass spectrometry from achieving both single molecule detection limits and the required level of quantification in order to catch disease signatures at the earliest possible stage of development with minute quantities of tissue or bodily fluids.

A second problem is that the very act of generating a gas phase sample of the specimen of interest, as required for mass spectrometry may lead to extensive fragmentation of the parent molecule. The various proteins in the body are all very similar, being composed of the same nucleotides and amino acid monomers. Excessive fragmentation makes it impossible to make unique assignments to molecular species. As long as one has a parent ion component, as a reference point, fragmentation patterns can aid in identification of the parent molecule.

Unfortunately, the fragmentation pattern needs to be highly reproducible and unique to a given molecule. If there is more than one possible molecular species present, then fragmentation leads to overlapping mass peaks and loss of identification. In order to identify proteins within an unpurified sample or directly from tissue, the fragmentation of the parent molecule be minimized as much as possible to avoid congestion in the fragmentation patterns and the fragmentation needs to induced in a controlled and known way. Otherwise, there will be too much overlap of common fragments to decipher the fragmentation pattern and identify the molecule of interest (e.g. a protein). Current mass spectrometry methods are unable to achieve such control over fragmentation, and therefore require the aforementioned onerous pre-analytic separation steps. For this reason, mass spectrometry has principally been confined to identification of highly purified samples.

This problem is exacerbated by the natural propensity for certain molecules to form aggregates, and is particularly severe in proteomics research where one is interested in quantitative information on the expression of certain proteins. However, these proteins often occur naturally in complexes or a distribution of isolated molecules and multiple complexes with different proteins involving complicated equilibria with several other protein complexes. Within a mass spectrometer, the ionization of protein complexes leads to fragmentation patterns or spurious mass to charge ratios that mask the identity of the molecule(s) of interest.

For this reason, most of the time involved in performing a proteomic assay involves the pre-analytic purification of proteins, which is achieved by batch processing relatively large amounts of material and using various complex and time consuming steps (such as chromatography and electrophoresis) to separate the initial mixture into highly purified protein components. The purified proteins are then injected into a mass spectrometer for identification. The purification step is required to enable identification of the protein by ensuring all mass fragments are from the same molecule.

Even with this step, quantification of the amount of protein present in the initial sample is simply not possible, for the reasons discussed above. Further, the need to purify proteins before subjecting the sample of interest to detection greatly reduces the efficiency or throughput of mass spectrometry. As a result, despite the inherently high sensitivity of mass spectrometry, large sample volumes are required in order to compensate for the downstream losses in the purification steps. To achieve the ultimate detection limits of mass spectrometry, in situ isolation and separation of molecular species of interest is required.

What is therefore needed is an improved method of sample preparation for mass spectrometry that delivers reproducible ionization and minimal molecular fragmentation required for quantitative and sensitive assays.

SUMMARY OF THE INVENTION

Embodiments of the present invention address the aforementioned obstacles in sample desorption and mass spectrometry sample preparation by providing methods and systems that enable improved reproducibility and a lower detection limit.

In one embodiment, the invention provides a method for the soft desorption of analyte from a sample, in which an optical beam absorbed within an irradiate zone of the sample causes vibrational excitations of a component within the sample. The optical beam is provided with sufficient energy to superheat the component, in which vibrational excitations rapidly transfer energy to translational excitations that drive the ablative desorption process. The optical beam is provided for a time interval that is less than the time duration required for the loss of energy out of the irradiated zone due to thermal diffusion and acoustic expansion. As a result, the energy deposited by the optical beam is primary provided to translational motion through the above process, resulting in the rapid ablation of the sample within the irradiated zone. Since the timescale for desorption is faster than that of the timescale for energy transfer from the component to the analyte within the sample, the analyte is desorbed via a soft ablation process in which the analyte is delivered into a gas phase substantially without ionization and fragmentation.

Accordingly, in a first aspect of the invention, there is provided a method of performing the soft desorption of analyte from a sample, the method comprising the steps of:

irradiating the sample with an optical beam; and optically exciting vibrational levels of a component of the sample within an irradiated zone;

wherein the sample is irradiated for a time interval that is less than a time duration required for energy loss beyond the irradiated zone to thermal diffusion and acoustic expansion; and wherein energy absorbed from the optical beam by the component is sufficient to superheat the component and cause the ejection of an ablation plume from the irradiated zone.

In a preferred embodiment, the ablation plume comprising desorbed analyte is ionized and directed towards the inlet of a mass analysis device such as a mass spectrometer. In one embodiment, the ablation plume is ionized within an evacuated region by a vacuum-ultraviolet optical beam that is directed onto the ejected plume. In another aspect of the invention, the ablation plume is ionized by a linear resonant process in which an optical beam is directed onto the ablation plume, where the optical beam comprises spectral content and a phase profile to selectively ionize the analyte by a resonant, one-photon process where electronic levels from an initial state to an ionization state are excited.

Accordingly, in another aspect of the invention, there is provided a method of preparing a sample for mass analysis, the method comprising the steps of:

irradiating a sample with an optical beam; and optically exciting vibrational levels of a component of the sample within an irradiated zone;

wherein the sample is irradiated for a time interval that is less than a time duration required for energy loss beyond the irradiated zone to thermal diffusion and acoustic expansion;

wherein energy absorbed from the optical beam by the component is sufficient to superheat the component and cause the ejection of an ablation plume from the irradiated zone;

ionizing the ablation plume with an ionizing means; and directing the ionized ablation plume into an inlet of a mass analysis device.

In another embodiment of the invention, there is provided a system for desorbing an analyte, wherein the sample comprises a component having an excitation spectrum comprising vibrational energy levels, the system comprising:

an optical apparatus for directing an optical beam onto a sample and irradiating an irradiation volume within the sample, the optical beam comprising:

a frequency spectrum for optically exciting vibrational levels of a component of the sample;

a time duration shorter that is less than a timescale required for energy loss beyond the irradiated zone to thermal diffusion and acoustic expansion; and sufficient energy to superheat the component and cause ejection of an ablation plume from the irradiated zone.

In a preferred embodiment, the system further comprises an ionization means for ionizing the ablation plume and a mass spectrometer for performing mass analysis of the ionized analyte, wherein the sample is positioned to direct the ablation plume through an inlet of the mass spectrometer. More preferably, the ionization means comprises a second optical apparatus for photo-ionizing the ablation plume.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Figure 1:
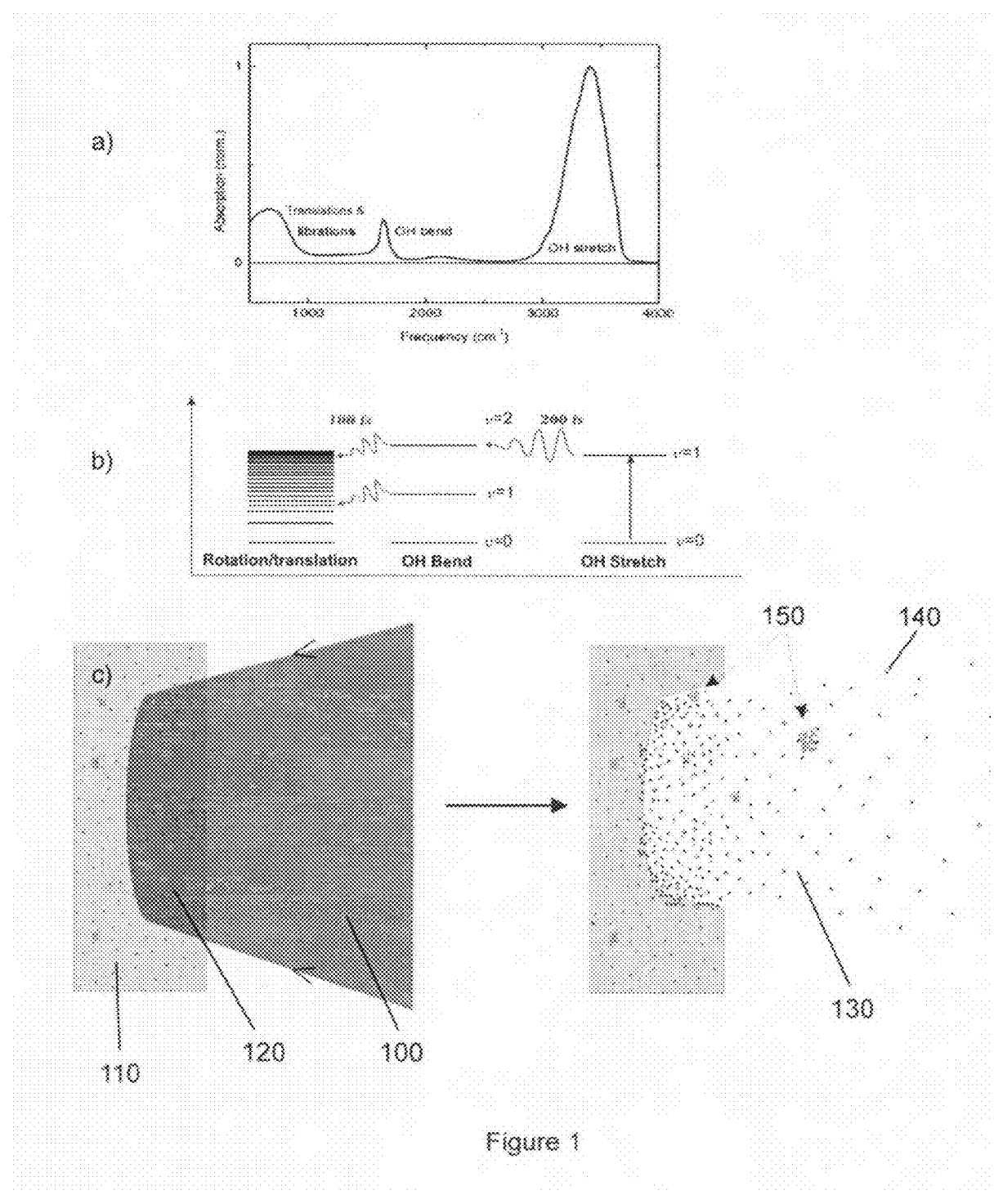
FIG. 1 illustrates the process of soft ablative desorption, where (a) shows the vibrational absorption spectrum of water, (b) illustrates the timescales involved in coupling between vibrational and translational states, and (c) illustrates the ablation of a liquid sample.

Without limitation, the majority of the systems described herein are directed to a process involving the soft ablative desorption of an analyte. As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to the soft ablative desorption of an analyte, in particular when the ablative desorption is achieved with water as an ablative propellant.

As used herein, the term "about", when used in conjunction with ranges of dimensions, temperatures or other physical properties or characteristics is meant to cover slight variations that may exist in the upper and lower limits of the ranges of dimensions as to not exclude embodiments where on average most of the dimensions are satisfied but where statistically dimensions may exist outside this region.

As used herein, the term "optical" means high frequency propagating electromagnetic waves, including, but not limited to, visible, infrared, ultraviolet and vacuum ultraviolet radiation.

In a first embodiment, the present invention provide a unique sample preparation method for the gas phase desorption of analyte, where the analyte is ejected from the sample in a state that is substantially free of fragmentation, ionization, and excitation. Before proceeding with the disclosure of embodiments of the invention, a discussion is provided below of the novelty and utility of the soft ablative desorption method for sample preparation that underlies several preferred embodiments of the invention.

Until recently, it was generally been believed that the only method for achieving laser ablation of a material without damaging the surrounding material was to use the shortest possible laser pulses. U.S. Pat. No. 5,720,894 to J. Neev et al. is a prime example of this school of thought in the art. This patent describes the use of ultrashort pulses from femtosecond to picosecond lasers to ablate materials through the excitation of electrons, electron avalanche effects creating nonlinear absorption to localize the light absorption, and subsequent plasma formation. In this scenario, the laser pulses are typically in the near infrared and visible wavelengths by which the light absorption promotes electrons to upper electronic levels of the molecule or bands in solid state materials. Effectively, the laser pulses are used to deposit enough energy through these excited electrons to highly ionize the material and create a plasma. The plasma in turn is no longer a bound state of matter and undergoes ablative release, driven by coulombic forces as well as the excess energy deposited in generating ions.

Under the strong femtosecond laser excitation conditions, the absorption of light is confined to a few hundred nanometers through nonlinear absorption by the material and resultant quasi-free electrons. Energy deposition by this method raises the lattice temperature to several thousand degrees to create the unbound plasma state of matter and subsequent ablation. This method requires the very strong absorption of the laser light to localize the energy deposition so the minimum amount of energy is used to drive ablation.

It is also important to recognize that in the aforementioned femtosecond laser ablation process, the energy is deposited in the electrons. The energy ultimately must go from the highly excited electrons into lattice phonons or mechanical vibrations of the host medium and subsequently into translational motions of the ablation process itself. This overall process takes many picoseconds to obtain lattice temperatures high enough to achieve ablation.

Furthermore, the use of electronic transitions under strong excitation conditions necessarily leads to multiphoton ionization, as an inherent part of the strongly localization of the light absorption. Multiphoton absorption indiscriminately generates very high densities of highly reactive ions in the formation of the plasma state, ionizing everything, and accompanied by almost complete disintegration of material. This indiscriminate ionization and massive fragmentation, to nearly bare atoms, leads to complete loss of molecular identity and renders this laser ablation mechanism useless for applications in mass spectrometry. As such, plasma formation can significantly impair repeatability and quantitation in mass spectrometry applications.

The aforementioned process, which involve the generation of highly excited electrons to drive ionization and ablation, is actually slower than the vibrational energy relaxation of water into translations. Energy transfer from electrons to phonons occurs through a process known as electron-phonon coupling and occurs on the picosecond timescale—over an order of magnitude slower than vibrational energy relaxation into translational motions of water.

This important distinction was realized by the present inventors and adapted for use as a method for of laser ablative material processing, as disclosed in U.S. patent application Ser. No. 11/321,057 corresponding to US Patent Publication No. 20060190572, titled "Laser Selective Cutting by Impulsive Heat Deposition in the IR Wavelength Range for Direct-Drive Ablation", which is incorporated herein in its entirety by reference. In this context, it was disclosed that the use of infrared excitation of water's vibrational modes can deposit energy effectively directly into ablative degrees of freedom and significantly faster than even the so-called cold ablation coined for the above femtosecond laser processing that exploits the excitation of electrons and quasi-free electrons.

The present invention arose from the realization and discovery that the aforementioned material processing ablative method, when applied to samples containing molecular analyte of interest, could be used to desorb analyte molecules without ionization or fragmentation.

Accordingly, by exploiting the efficient coupling of absorbed energy in the infrared to translational modes, it is possible to overcome the deficiencies of the use of femtosecond laser ablation based on electronic transitions and obtain a soft ablative desorption process substantially free of ionizing radiation effects.

According to embodiments of the present invention, one explicitly takes advantage of the mode specific vibrational spectrum of a component of the sample, such as water, to selectively deposit energy into an intramolecular vibrations that effectively go directly into the required translational modes for ablation and desorption. This method can be equally applied to other molecules that also undergo vibrational energy relaxation to translational motions. Water is the prime example as it is the largest constituent of most biological samples and undergoes the fastest energy conversion. While the forthcoming disclosure focuses on primarily on water as the sample component driving ablative desorption through vibrational absorption, it is to be understood that other molecular components having vibrational excitations within a material can also serve as the component for driving soft ablative desorption according to embodiments of the invention. For example, in a non-limiting example, amide vibrations, phosphate bands, C—H stretch/bends may be used.

In a preferred embodiment of the invention, energy from an optical beam is deposited into water within a sample, causing the ejection of an ablation plume that propels very large molecules into the gas phase on timescales faster than energy can be transferred from the hot water molecules to the analyte of interest and thus introduce analyte molecules into the gas phase with the least amount of excess energy possible. As a result, this method of soft ablative absorption (preferably driven by a laser or other intense optical source) is a gentle method for desorbing large biomolecules into the gas phase.

This aspect is important, because in many analytical techniques, it is preferably to deposit minimal amounts of energy into the analyte prior to detection, as the deposition of large amounts of energy to the analyte can often lead to uncontrolled fragmentation and loss of the ability to identify the analyte, especially in a mixture of different molecules.

For example, in applications involving mass analysis, in which the analyte is subsequently ionized, the presence of the so called parent ion (the original molecule minus a single electron) is very important to proper identification of molecules. The fragmentation pattern is also important but should be as narrow a distribution as possible to avoid overlap with other possible species.

The extremely strong absorption of water is another important aspect of methods according to the invention. This feature leads to strong localization of the absorbed energy, which is useful in minimizing excess heating effects. Accordingly, very little energy per pulse is required to superheat water well above its vaporization point and have it undergo an impulsive ablation process. For example, pulse energies using as little as 100 microjoules per pulse for a 100 micron focus are sufficient to drive molecules into the gas phase due to the inherent large absorption cross sections in the infrared part of the absorption spectrum and the low gas phase transition temperature of water. In this scenario, the energy remains primarily in the highly excited water molecules. In an equally important aspect, the ablation process can be readily controlled so as to not involve any multiphoton ionization. Effectively, energy is deposited selectively into water to act as a propellant to drive molecules into the gas phase.

It is noted that most biological samples comprise a significant concentration of water (human beings are made up of 60% water), and of all human constituent matter, water has the lowest boiling point or phase transition to gas phase. Water is therefore a preferred component to act as a propellant for soft ablative desorption. It has an incredibly fast energy deposition process into the correct degrees of freedom for ablation as discussed above. The fact that it has a fairly low boiling point means that water can be impulsively driven into the gas phase, propelling all molecules within the heated volume also into the gas phase, at low enough lattice temperatures to avoid collateral damage or burning of adjacent material. The publication, M. L. Cowan, B. D. Bruner, N. Huse, J. R. Dwyer, B. Chugh, E. T. J. Nibbering, T. Elsaesser, and R. J. D. Miller, "Ultrafast Memory Loss and Energy Redistribution in the Hydrogen Bond Network of Liquid $H_2O$," *Nature* 2005, 434(7030), 199-202, describes the dynamics of energy distribution of $H_2O$ and the loss of frequency correlations in pure water. It was learned that vibrational motions of water are strongly coupled to librations (hinder rotations) and energy flows from the vibrations to translational degrees of freedom, hindered rotations and molecular velocities on an incredibly, 100 femtosecond, fast time scale. The key realization was that this fast relaxation is going into the very same motions involved in ablation on a 100 femtosecond time scale. The coupling of light energy into translational motion is faster in water than in any other material.

Accordingly, in a first embodiment of the invention, there is provided a sample preparation method in which an analyte is desorbed from a sample. Uniquely, the present embodiment desorbs the analyte using a soft ablative desorption process that generates gas-phase analyte that is substantially unfragmented and uncharged from a solid or liquid sample. As will be discussed in detail below, the desorption method according to embodiments of the present invention differs from prior art methods by several fundamental distinctions.

The analyte is desorbed from the sample by a soft ablation process in which an optical beam is directed onto the sample, where the optical beam is absorbed by the sample, causing the direct vibrational excitation of a component of the sample. This is achieved by selecting the spectral content of the optical beam to overlap with one or more vibrational absorption of the component within the sample. The component of the sample is preferably present in a sufficiently high concentration to cause strong vibrational absorption within a local irradiated zone.

Unlike prior art methods, the optical beam is directed onto the sample for a time interval that is less than the time duration over which energy is lost beyond the irradiated zone to thermal diffusion and acoustic expansion. Furthermore, the optical beam is provided with sufficient intensity to cause the component of the sample to be superheated and to rapidly couple the absorbed vibrational energy into translational motion before energy can be lost outside of the irradiated zone. The superheated component drives the ejection of an ablation plume from the irradiated zone, and analyte within the irradiated zone is rapidly desorbed into the gas phase.

The rapid ablation of the sample material within the irradiated zone has the important benefit of driving the analyte into the gas phase in a substantially unfragmented state, in which its native electrical charge state is largely preserved. Furthermore, the rapidity of the ablation step produces gas phase analyte before sufficiently time has elapsed for the component to produce heating and excitation of the analyte, thereby providing desorbed analyte with very low energy.

Preferably, the optical beam is provided by a laser or amplified laser that delivers an intense optical pulse to the sample. Since most vibrational bands absorb optical power in the infrared spectrum, the optical source is preferably an infrared source tuned to the vibrational absorption of the one or more components within the sample.

In the specific and non-limiting case in which the absorbing component of the sample is water, the optical beam is used to produce superheated water molecules above the gas phase transition that in turn serve as the propellant for driving molecules within the aqueous environment of the sample into the gas phase intact or the original charged state for molecular ions. The soft ablative desorption mechanism is preferably employed using infrared laser pulses in the 100 femtosecond to 1 nanosecond range, in which case the ablative desorption process occurs faster than substantial or complete energy transfer can occur from the hot water molecules to the biomarkers of interest to minimize thermal fragmentation as much as possible.

Figure 2:
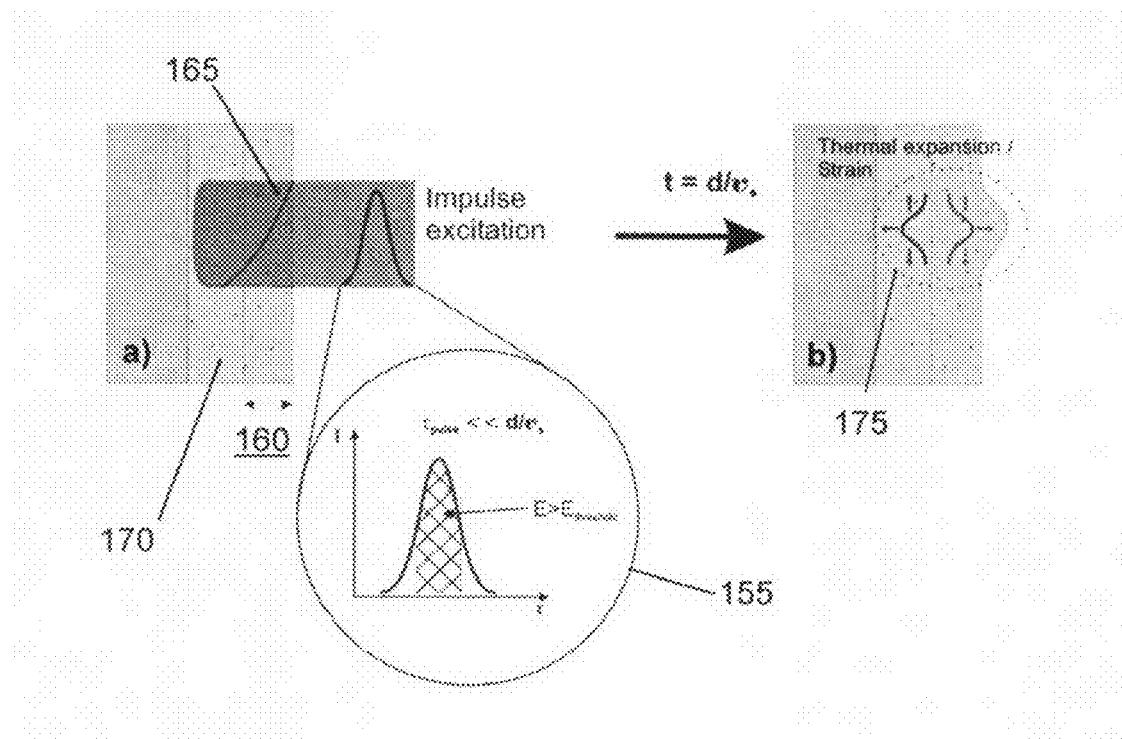
FIG. 2 illustrates the pulsewidth and absorption depth of an optical pulse employed for soft ablative desorption.
Figure 3:
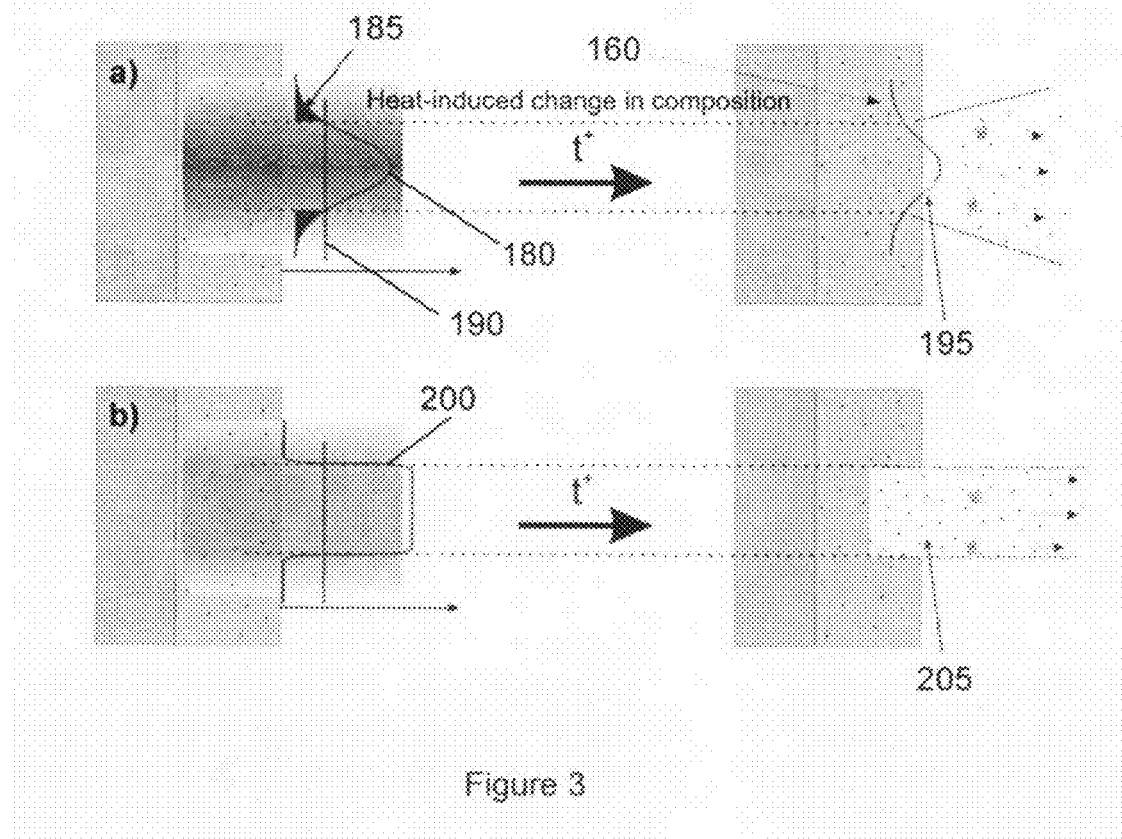
FIG. 3 illustrates the effect of the spatial profile of the optical beam on the ablation plume and surrounding material.

The mechanism and basic concepts underlying this embodiment are depicted in FIGS. 1 to 3. FIGS. 1(a), 1(b) and 1(c) show the general features of the first embodiment, in which analyte molecules are desorbed to the gas phase through soft ablation. This figure illustrates the general process of soft ablative desorption, in which a well-defined plume of gaseous molecules is generated by ultrafast relaxation of vibrational energy into translational degrees of freedom following direct vibrational excitation with an optical source beam.

Specifically, FIG. 1(a) shows the spectrum of water as an exemplary yet non-limiting target molecule for selective energy deposition into vibrational excitations. This figure clearly identifies the key vibrational bands that can be directly excited via an infrared optical source, such as an infrared laser or infrared amplified laser system. The time scales for conversion of the initially localized energy in molecular vibrations to translational motions needed for ablation is shown in FIG. 1(b) for the case of water. The relaxation is on the femtosecond scale, illustrating that the water temperature can be driven well above the phase transition temperature and stability point, enabling the water to act as a propellant for desorbing analyte in the water into the gas phase. Notably, due to the extremely rapid time scale in which the deposited energy is converted directly into translational energy of the sample component acting as the propellant (i.e. water), the desorption process is faster than the timescale over which energy exchange can occur between the translationally hot water molecules and desorbed analyte (for example, proteins).

This process is illustrated in FIG. 1(c), where an optical beam 100 tuned to a vibrational absorption band of water is incident on the sample 110 and absorbed by water within a local irradiated zone 120 (typically on the order of 1 micron for samples having a large concentration of water). In the case of water, the optical beam is preferably tuned to excite either OH stretching vibrations in the 3000-3600 $cm^{-1}$ range (approximately 3 micron wavelengths), OH bend modes in the 1500 $cm^{-1}$ to 17000 $cm^{-1}$ range (6 micron wavelengths) or other combinations of intramolecular and intermolecular vibrational bands. The optical beam is provided for a time interval that is less than the time duration over which energy is lost beyond the irradiated zone to thermal diffusion and acoustic expansion—for example, less than 1 ns for the case of water. During that time interval, sufficient energy is delivered (for example, in the case of water, 100 microjoules or more) to cause the water within the irradiated zone to be superheated. This in turn leads to the ablation of the sample within the irradiated zone, producing a gas phase ablation plume 130 that includes both water 140 and analyte 150 that was present in the irradiation zone. Preferably, the desorbed analyte is then measured in an analytic method such as mass spectrometry, preferably using photo-ionization, as further discussed below.

While the figure shows protein as the desorbed analyte 150, it is to be understood that a wide range of molecules may be desorbed according to embodiments of the present invention, including, but not limited to, small molecules, nucleic acids, large and small proteins and non-biological molecules such as organic and inorganic, and any molecular species and/or atomic clusters.

Here it important to note that vibrations are highly specific to a particular molecule. By explicitly exploiting this property, an optical source such as an ultrafast infrared laser can be tuned in wavelength to selectively excite a particular component (e.g. a specific molecule such as water) within the sample to be ablated. The energy relaxation pathway for water is shown as a non-limiting exemplary case.

As noted above, to produce soft ablative desorption, the amount of energy deposited into the irradiation zone is sufficient to superheat the absorbing component (for example, this can be achieved by driving the lattice temperature approximately 1.5 times higher than the temperature of the gas phase transition for the component to ensure the phase transition occurs within the impulse limit).

Provided that the optical beam is incident on the sample for a time duration that is shorter in duration than the time for material expansion over the excited volume element, the energy deposited thermally will go into driving the soft ablation process. The dynamics of the ensuing phase transition for superheated materials occur on picosecond time scales, i.e. faster than the speed of sound limited thermal expansion. In this manner, the thermal gradients are largely normal to the surface and a relatively well defined column of molecular species are introduced into the gas phase. As discussed below, this mechanism of introducing molecules into the gas phase can be used as a sample preparation step for any conventional mechanism for generating ions for molecular detection with mass spectrometry (such as corona discharge or electrospray) in order to improve sensitivity while simultaneously providing spatial resolution.

FIG. 2(a) shows the temporal properties of a preferred embodiment in which the optical beam comprises an optical pulse (such as an infrared laser pulse) for soft ablative desorption. The figure inset 155 shows temporal characteristics of the pulse, whereby the pulse duration is less than the time for thermal expansion of the excited volume element. The incident optical beam is absorbed over an absorption depth range 160 defining an irradiated zone 165, over which the majority of the optical power is absorbed (a small percentage of power is absorbed further in the sample with the secondary zone 170).

In FIG. 2(b), a process is shown in which an excited volume element 175 expands at the speed of sound limit. This acoustic expansion process reduces the material stresses, and reduces the available force to drive the ablation process.

Therefore, in a preferred embodiment, the optical beam comprises a pulse having a duration less than the time it takes for material expansion, and ideally should be shorter than the time it takes for energy exchange between the superheated absorbing component and the analyte to be desorbed. In a preferred embodiment, the absorption depth will be on the order of a micron, such that the pulses should be less than about 1 ns in duration in biological samples comprising a large water concentration. Preferably, the pulses should be long enough to keep the peak power of the electric field small enough to avoid multi-photon ionization.

In a preferred embodiment in which the energy deposited by the optical beam exceeds the bound potential of the component (e.g. the bound potential of a lattice) by more than approximately 50%, the entire process of driving molecules into the gas phase occurs on picosecond time scales. Effectively, the superheating of the component driving ablative desorption leads to an explosive, ablative, phase transition on a picosecond timescale. As noted above, this phase transition process is made to occur faster than energy can be lost to thermal expansion. In this scenario, the vibrationally absorbing component effectively acts as a propellant to drive any molecules contained within the irradiated zone to be injected into the gas phase intact as neutral species. The time scale for the overall process is such that the molecules of interest with respect to detection enter the gas phase with the least amount of excess energy possible.

FIG. 3 shows examples of the spatial characteristics of the source beam. A Gaussian beam profile 180 is shown in FIG. 3(a), where a portion of the beam 185 does not delivery sufficient energy to super heat the sample component acting as a propellant. This threshold is shown by the dashed line 190. This effect results in unnecessary heating of the sample at the edges of the irradiated zone, where the sample component does not reach a sufficiently high temperature to support ablative desorption. As a result, the ablated plume 195 is not ejected as a collimated molecular beam and collateral damage of the sample may occur.

Accordingly, as shown in FIG. 3(b), a flat top profile 200 for the laser is preferred over a normal Gaussian laser beam to avoid collateral damage due to heating of adjacent material that does not reach the ablation temperature (indicated by dash line) and to keep the thermally derived forces substantially normal to the surfaced to generate as collimated a molecular beam 205 as possible. The present method therefore involves directing an incident optical beam (preferably a short infrared pulse) tuned to 1-photon vibrational resonances to deposit energy into the irradiated zone as heat (translational/rotational motions) on a timescale that is faster than that over which either thermal diffusion or acoustic expansion can transit energy outside of the irradiated zone. This new mechanism solves the problem of desorbing large molecules into the gas phase without fragmentation and presents them as perfect targets for quantitative photoionization, as discussed below.

As noted above, by providing an optical beam (preferably a laser pulse) shorter than the time for thermal expansion of the excited volume, there no substantial energy loss to expansion and the energy is most efficiently converted to translational motion and disruption of the forces restraining the molecules in the condensed phase. The absorption depth of the absorbed infrared light energy in water vibrational modes of biological samples is typically less than 1 micron in depth (1/e) due to the strong absorption of liquid water. For typical speeds of sound for biological tissue and water, the time for thermal expansion of a micron thick excited volume is on the order of 1 ns. The speed of sound in water, as a lower bound, is $1.5 \times 10^5$ cm/sec such the time for thermal expansion of a 1 micron thick heated region is $1 \times 10^{-4}$ cm/$1.5 \times 10^5$ cm/sec=$0.7 \times 10^{-9}$ sec. According, in a preferred embodiment of the invention, the component acting as an ablative propellant is water, the optical beam is tuned to a water vibrational absorption band in the infrared (for example, at a wavelength of 3400 cm$^{-1}$), and a pulse having an energy of approximately 100 microjoules and a pulsewidth between about 100 fs and 1 ns is focused to a spot size of the order of 100 microns (e.g. the average diameter of the optical beam on the sample is preferably about 50-200 microns).

Thus, by using pulses of duration less than 1 nanosecond (ns), and preferably less than 100 picosecond (ps), it is possible to cause water to superheat, and transfer energy into translation energy, with sufficient amplitude to overcome the binding potential of the material. While examples above have disclosed the use of optical pulses for the delivery of the optical beam energy, it is to be understood that the temporal nature of the optical beam can take on a wide variety of forms, provided that the overall time duration criterion is respected. In a preferred embodiment, the optical beam is a Gaussian single pulse emitted by a laser or laser amplifier. However, in other embodiments, for example, the optical beam may be delivered as a series of intensity spikes of arbitrary complexity.

Figure 4:
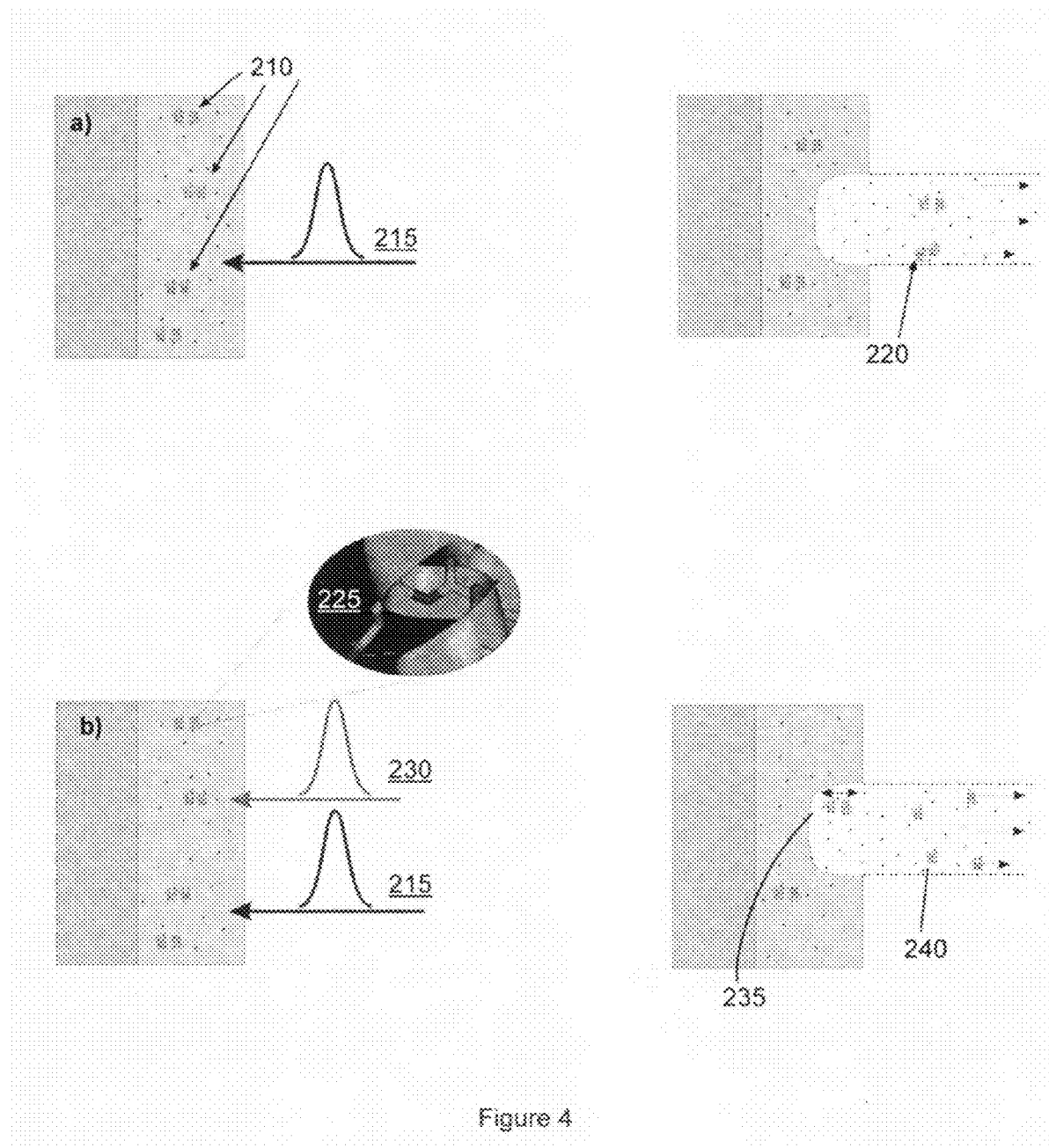
FIG. 4 shows (a) the desorption of analyte bound in a complex, and (b) the use of a second optical beam to dissociate the desorption of analyte bound in a complex, and (b) the use of a second optical beam to dissociate a complex prior to desorption.

The ablative desorption method is further illustrated in FIG. 4 for the case of water and for samples in which the analyte resides in the form of weakly bound complexes 210. Specifically, FIG. 4(a) illustrates wavelength tuning for molecularly selective ablation, in which vibrational stretching modes of water within the sample are directly excited by an incident optical beam 215 that is spectrally tuned to the infrared vibrational absorption of water at λ~3400 cm$^{-1}$. This results in "cold" ablation of the sample within the irradiated zone, and ablative desorption of analyte 215 in the sample as intact complexes 220. As noted above, the highly energized water molecules act as a propellant to drive even large biological molecules into the gas phase intact faster than energy exchange between the hot water molecules and proteins/biomolecules. Even large complexes can be introduced into the gas phase in this manner as minimal thermal energy is transferred to the complexes that would otherwise lead to dissociation of the complexes.

FIG. 4(b) shows a "warm" ablative desorption process for the combined desorption and dissociation of molecular complexes. This figure shows schematically tuning the wavelength of an additional optical beam 230 (for example, the wavelength of an additional infrared pulsed laser) to specifically excite proteins that are known or expected to reside within the sample. For example, the complexes may be protein complexes can be dissociated by breaking the amide bond as shown in inset 225, and the wavelength of the additional optical beam may be 1600 cm$^{-1}$ (more preferably, a non-covalent bond is broken to avoid fragmentation by selecting a frequency on resonance with the interface). This process is preferably performed in combination with the ablative desorption method described above, resulting in the desorption and disassociation of molecular complexes (shown as disassociating at 235) within the sample, thereby producing dissociated analyte molecules 240 in the ablation plume. This excitation mechanism deposits energy into the target molecular complex, causing it to dissociate into its individual molecular components. In a related embodiment, by using a cold ablation process, followed by a separate warm ablation process on identically prepared samples, molecular complexes can be uniquely identified.

Accordingly, in an embodiment of the invention, one or more additional optical pulses are provided tuned to other vibrational modes of a molecular complex within the sample, where the molecular complex comprises an analyte of interest. This allows energy to be added to complex selectively to provide enough energy to untangle analyte from the complex, whereby isolated analyte molecules can be ablatively desorbed in an untangled state.

In certain embodiments, the sample may comprise all of or a portion of biological samples including, but not limited to, tissue, cells, organs, bodily fluids, urine, blood, serum, plasma, cerebral spinal fluid, and sputum. In certain applications, it is highly desirable to prepare a sample directly from a solid or semi-solid substance such as biological tissue. There are also applications in spatially resolved analysis of solids and heterogeneous solid solutions such as frozen samples. More preferably, the samples are sliced so that the thickness of the sample is approximately equal to the absorption depth of the incident optical beam. In a non-limiting example in which the sample is biological tissues, the tissue is preferably thinly sliced to thicknesses on the order of 1-10 microns to avoid large secondary plumes, which can cause problems when coupling the ablative plume to an analytical device such as a mass spectrometer.

Slicing of tissues in thin micron sections is an established procedure using either cryogenic freezing or bonding in epoxy and using a microtome. The smallest example one may consider is likely the dissection of a single cell. In a preferred embodiment, soft ablative desorption is perform directly on cells, and the cells are prepared with a thickness on the order of 1 micron, i.e., approximately the absorption depth of an infrared optical beam tuned to a water vibrational absorption band.

Certain materials are too fragile to be exposed to the extremely high stresses generated during impulsive heat deposition. There are also certain molecular systems that will aggregate during the photoionization step or, undergo undesired reactions upon ion formation. In such cases, the density of the optically driven plume needs to be maintained at a lower density with much slower release of the molecules to the gas phase. To accomplish this, the optical beam tuned to selectively deposit energy into the host medium is stretched in time to maintain the lattice temperature just at the boiling point. This can be accomplished by a pulse with a fast rise time followed by a trailing pulse profile that compensates for thermal diffusion from the excited volume. The molecules will effectively boil off over timescales ranging from nanoseconds out to many microseconds to keep the density of molecules in the gas phase as low as possible.

However, there is a trade off. The molecules enter the gas phase at the same temperature as the lattice rather than a "cold" ablation. Water in this case is the preferred host medium as the relatively low boiling point avoids excessive thermally induced fragmentation. This prescription gives the most gentle release of the molecules of interest to the gas phase possible while still exploiting the basic elements of this invention, multiplexing IR and VUV or UV/Vis pulses for enhancing the detection of the molecules of interest by mass spectrometry by several orders of magnitude over present methods. This prescription prevents fracture and undesired gas phase reactions subsequent to photoionization by minimizing collision frequency.

Figure 5:
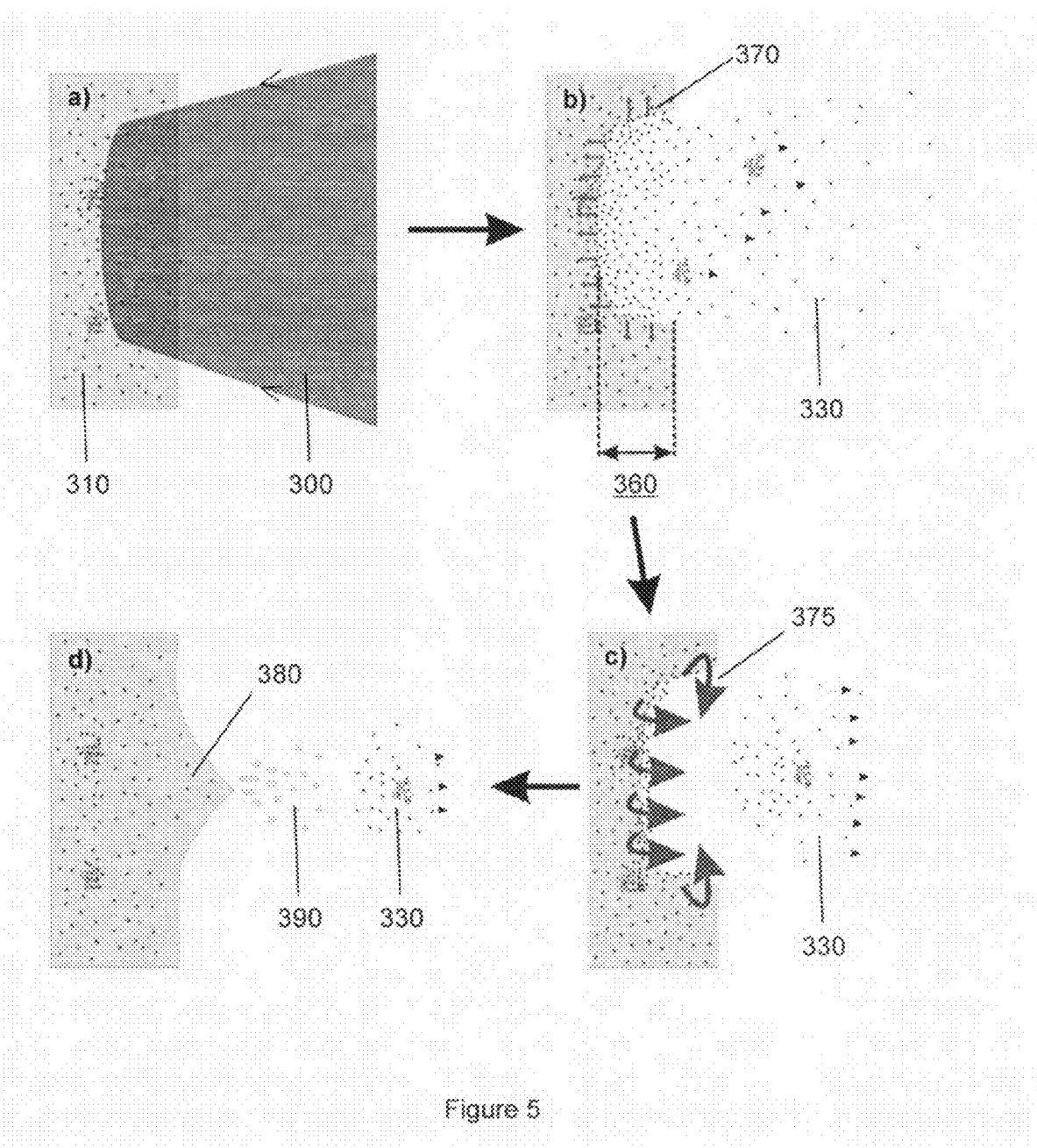
FIG. 5 illustrates, sequentially through frames (a)-(d), the process of recoil for an optically thick sample.

FIG. 5 illustrates the process of soft ablative desorption with a liquid sample and the effect of sample depth of the ablation process. In FIG. 5(a), an optical beam 300 is absorbed by sample 310 as described above. The aforementioned soft ablative desorption process, shown in FIG. 5(b), drives the liquid sample into the gas phase, producing ablation plume 330. However, sample 310 is an optically thick sample, i.e., the sample thickness is greater than the absorption depth of the optical beam. As a result, forces 370 are applied to the remaining sample as the ablation plume is ejected. In FIG. 5(c), recoil forces 375 are generated as the ablation plume 330 leaves the sample, and these forces generate sample recoil as shown in FIG. 5(d). The recoil causes a liquid cusp 380 to form, leading to the generation and ejection of nano-droplets 390 that follow the ablation plume 330.

Therefore, with a sufficiently short duration of the optical beam (for example, an infrared laser pulses) applied in the above prescribed manner, the material is ablatively desorbed with high velocities such that shock waves in the air and secondary propagation of the shock wave to the host medium occur. This side effect is preferably minimized in order to avoid additional (and potentially significant) amounts of material from being ejected along with the ablation plume, for example, in the form of droplets, large clusters or other aggregates. Such aggregates potentially mask the identity of and/or signal from desorbed analyte of interest and may lead to nonlinear effects that hinder quantitative analysis.

It is therefore beneficial to avoid such effects by preparing a liquid sample in a sampling device in which the thickness of the sample is of the same order as the absorption depth of the optical beam. This enables an increase the efficiency of analysis systems without the need to characterize the dynamics of the ablation plume, as well as reducing the amount of sample required for the analysis. This is especially challenging for water samples, where the absorption depth of infrared light by vibrational states is limited to only a few microns, and where losses due to evaporation can be problematic.

Figure 6:
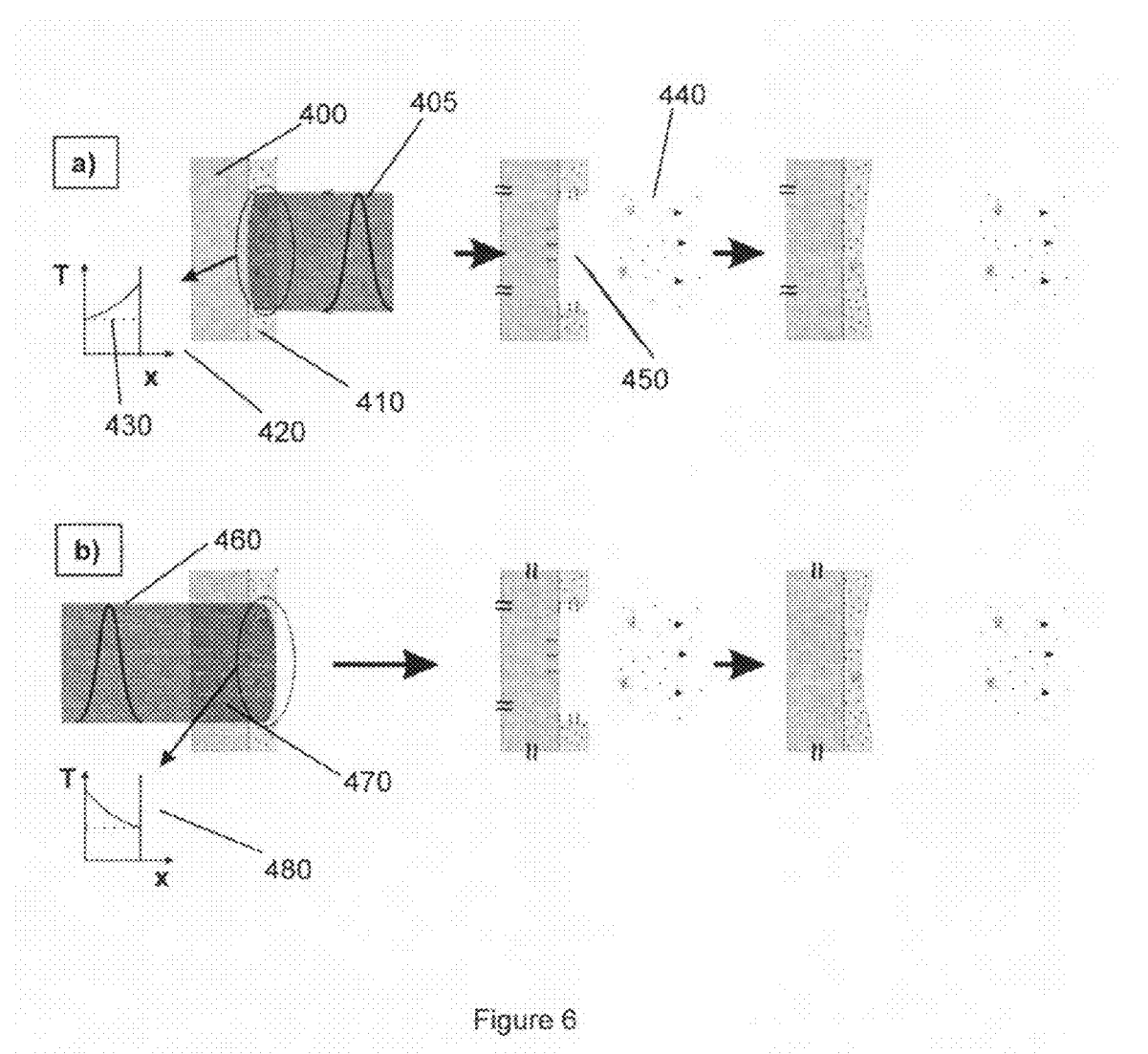
FIG. 6 shows arrangements for the (a) front and (b) rear optical excitation of an optically thin sample housed in a sample holder.

FIG. 6(a) illustrates a preferred embodiment of the invention in which a liquid sample is prepared in a thin film a thickness approximately equal to the absorption depth of the optical beam 405. The sample is contained on a surface 400 that is preferably transparent to the optical beam to avoid potential damage to the surface from the optical beam. The sample forms a thin film 410 and the optical beam incident on the sample superheats the absorbing component within the sample that acts as the ablative propellant, producing a temperature profile shown at 420, with temperatures within the irradiated zone of the sample exceeding a threshold temperature 430 for ablative desorption. This leads to essentially the full thickness of the sample being ablated, resulting in a substantially recoil-free ablation plume 440 and an ablated void 450 that resolves laterally without substantial recoil.

A preferred embodiment is shown in FIG. 6(b), where the optical beam 460 is directed onto the sample from behind, where it propagates through a transparent surface 480 and impinges on the sample at the point of contact between the sample and the surface. The absorption of the optical beam by the component within the sample acting as the propellant generates a temperature profile 480 that is the reverse of the corresponding profile 420 shown in FIG. 6(a). As in FIG. 6(a), the irradiated zone comprises substantially the full sample thickness, and the ablative desorption process occurs substantially without recoil.

In a preferred embodiment, the surface upon which the thin layer of sample is supported is preferably a hard material and more preferably a material that does not significantly absorb at the wavelength of the optical beam. Exemplary yet non-limiting materials include $SiO_2$, silicon, and sapphire. A hard substrate having a much higher vaporization temperature than the solvent thus serves as a hard boundary condition for ablative desorption process so that any shock waves generated in the excited volume of sample are merely reflected rather than leading to secondary mass ejection.

Those skilled in the art will readily appreciate that the absorption depth of the optical beam can be determined by a variety of methods; for example, by measuring the transmission of light through a known sample thickness at the desired frequency, or by measuring a transmission spectrum of the sample using an analytical instrument such as a spectrometer.

Therefore, in a preferred embodiment, a liquid sample is prepared for soft ablative desorption in a microwell having a thickness on the order of the absorption depth of the optical beam within the sample, where the material in which the microwell is formed is preferably a hard material and more preferably a material that does not significantly absorb at the wavelength of the optical beam. Such a method of sample preparation is well suited for subsequent analysis of desorbed analyte by mass spectrometry, as discussed further below.

A preferred sampling device is disclosed in co-pending U.S. Provisional Patent Application Ser. No. 61/300,623, titled "Fluidic Sampling Device and Method of Use Thereof", filed Feb. 2, 2010, which is herein incorporated in its entirety. Briefly, the sampling device comprises a planar surface having a well defined therein, in which the hydrophilicity of the surface is greater than the hydrophilicity of the well side wall, such that the well structure is may be selectively wettable by liquid on the surface when the liquid is contacted with the top of the well. This preferred embodiment enables the controlled wetting and capture of liquid in wells having a wide range of aspect ratios (of width to depth), for example, exceeding one hundred. The well depth is preferably on the micron scale for producing stable yet thin liquid samples, as desirable for use in conjunction with the preceding embodiments of the present invention involving soft ablative desorption methods. The device preferably comprises an array of such wells for the preparation and subsequent analysis of a plurality of liquid samples.

Figure 7:
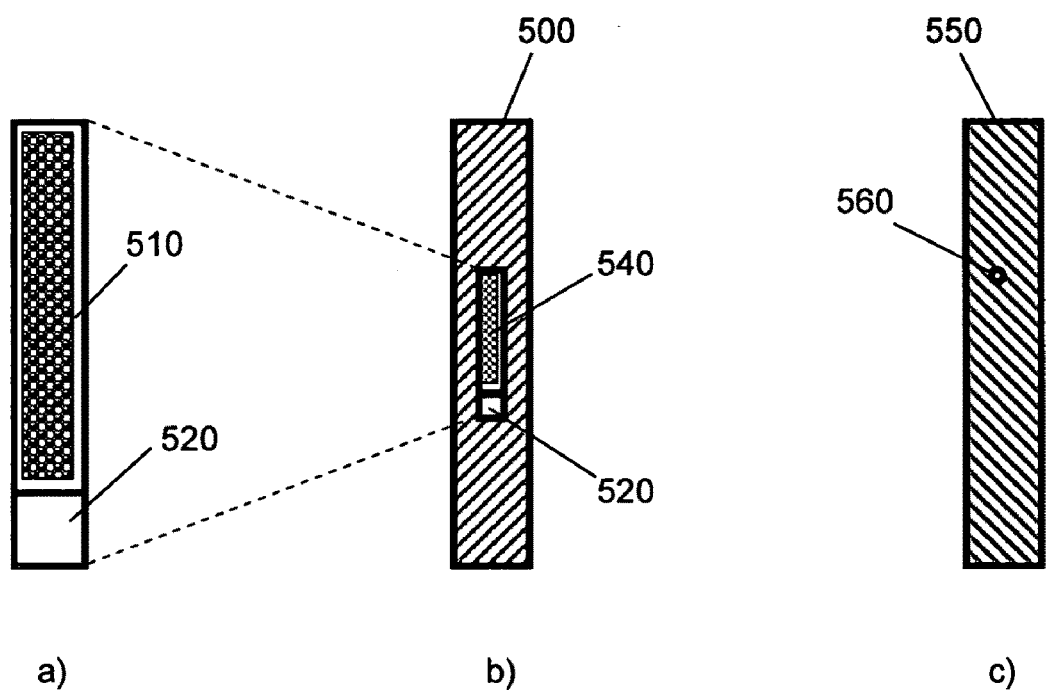
FIG. 7 illustrates a housing for enclosing a sample holder while providing external access to enclosed wells.

U.S. Provisional Patent Application Ser. No. 61/300,623, further discloses an apparatus for enclosing a microwell sampling device, which is well suited for various aspects of the present invention. The apparatus, which is shown in FIG. 7, preferably comprises a supporting platform 500 into which a fluidic chip 510 having one or more wells is placed. FIG. 7(a) provides a detail view in which the fluidic chip can be seen. The fluidic chip can be any fluidic chip having compatible with the soft ablative desorption method described above. Furthermore, those skilled in the art will appreciate that the chip could house a single well or an array of wells.

Included in the platform is a saturating reservoir 520 that is provided to maintain vapor pressure within the chip holder when the holder is closed by lid 550. This design provides a saturating environment when the wells are enclosed within the chip holder, preventing evaporation and maintaining a stable meniscus within the wells. The reservoir may be provided in any internal region of within the chip holder, and alternatively may be integrated within the chip itself for use within the chip holder. The reservoir may be filled with any liquid that can maintain an appropriate vapor pressure within the housing. Preferably, the reservoir is filled with a liquid that is substantially the same as the particle-containing liquid. In several non-limiting examples, the liquid provided to the reservoir may be a sample liquid, a buffer, or a sample supernatant.

The chip holder is covered by a slidable lid 550, which includes aperture 560 for permitting access to the chip. Lid 560 has sufficient cross-sectional area to maintain coverage of all other wells within the chip when translating the lid relative to the fluidic chip. While the embodiment shown in FIG. 7 illustrates a chip holder with a two-dimensional array of wells, which would be accessed by translating lid 550 in a two-dimensional plane relative to fluidic chip 510, the fluidic chip may comprise a linear array of one or more wells that are accessed by translating lid 550 in one dimension.

In a preferred embodiment, aperture 550 is sufficiently large to deliver fluid for filling a single well. Fluid may be delivered to the well using a variety of means known in the art, such as direct pipetting, or dispensing using an automated system such as a syringe pump. However, in a preferred embodiment, a well residing in the chip may be wetted by contacting a droplet of fluid with the chip surface, and translating the droplet relative to the chip so that it contacts the top of a well and fills the well according to a dynamic wetting process. In a more preferred embodiment, the dynamically filled well is provided according to the embodiments in U.S. Provisional Patent Application Ser. No. 61/300,623, where the upper chip surface has a hydrophilicity exceeding that of the well side wall.

Wells may be dynamically wet by translating a droplet along the upper chip surface, for example, by translating one or both of the chip and the fluidic source. In one non-limiting embodiment, a dynamically wettable well is filled by translating the aperture adjacent to a well, exposing the well and a portion of the upper surface in the vicinity of the well, contacting at least a portion of a fluidic droplet with the upper surface, and translating the droplet relative to the upper surface to contact the top of the well. The contact of the droplet with the top of the well transfers at least a portion of the droplet volume into the well. Translation of the lid, chip, and/or dispensing device may be achieved using motorized translation stages and devices known in the art, such as linear translation stages driven by linear motors.

In a preferred embodiment, the droplet is a partial droplet formed at an aperture of a fluidic dispensing device, such as a hemisphere, which may be contacted with the upper surface and removed from the upper surface after filling a well without wetting the upper surface. This can be achieved by selecting a fluidic dispensing device that supports droplet adhesion relative to the upper surface, such as a standard pipette tip.

After having filled a single well, additional wells may be filled with the residual fluid within the droplet by translating the chip relative to both the aperture 560 and the fluidic dispensing device, thereby moving the droplet along the upper chip surface. An additional well may subsequently be filled by contacting the droplet with the top of the additional well and dynamically filling the additional well.

In a preferred embodiment, the fluidic device may comprise a capillary filled with a fluid to be dispensed into one or more wells, as disclosed in U.S. Provisional Patent Application Ser. No. 61/300,623. For example, in one non-limiting embodiment, the capillary may form a component of a separation system such as a capillary electrophoresis system, where the serial dispensing of liquid into an array of wells enables a mapping of separated components within the capillary into an array of wells. With a known flow rate of dispensing into the wells, measurements from a given well can be correlated with a longitudinally separated segment of the capillary. In another non-limiting embodiment, the capillary may reside within sampling device such as a fingerstick blood sample device, and the dispensing of blood within the capillary into the array of wells may be used to generate a precise spatial array of aliquots for subsequent analysis. The capillary may comprise a wide range of capillaries known in the art, such a fused silica capillary.

A well residing on a chip may be filled from the capillary as follows. A pressure gradient is applied to the capillary and at least a partial droplet is contacted with the upper chip surface. As described above, a well may then be dynamically filled by translating the droplet along the upper surface until it contacts the top of a well. Preferably, multiple wells in an array of wells are filled according to the aforementioned method whereby the chip is subsequently translated relative to both the aperture and the capillary, enabling the droplet to be translated and contacted with additional wells. As noted above, this enables the aliquoting of liquid in a capillary into a two-dimensional array of wells.

In another preferred embodiment, a chip filled and housed within a chip holder may be stored and/or processed (for example, frozen or thermally incubated) and prior to a soft ablative desorption step. The subsequent soft ablative desorptive step (and any additional analytic steps) is preferably achieved by providing access to pre-filled wells on a well-by-well basis via the translation of lid 550, where aperture 560 may be selectively translated to provide access to a single well.

In aforementioned embodiments of the invention, methods have been provided for the ablative desorption of an analyte within a sample. However, the case may arise where one desires to measure a system of interest having an unknown composition, and possibly a heterogeneous composition. For such systems, it may indeed be the underlying composition of material that is of interest. For example, this may be the case for the exploration/characterization of a new tissue type. In such a case, biomarkers of interest may be entangled within protein complexes, and may become entrained in the various membranes and gel-like features of any intermixed cellular components during the soft ablative desorption process. The complexes need to be separated into their constitutive molecular components. In certain cases, the molecule of interest undergoes undesirable chemical reactions in the process of using denaturants. There are also many cases when one wishes to use solid tissue and analyze for disease states at specific locations in the tissue.

To achieve this separation, the soft ablative desorption process described above may be employed in a two-step ablative process to achieve separation of constituent molecular components. This approach avoids time consuming, and often wasteful, purification steps that require large amounts of material. A second ablative step may be needed for selected applications, notably in proteomics research and direct sampling of tissue other than bodily fluids.

Accordingly, in a preferred embodiment, a first soft ablative step is performed according to an aforementioned embodiment of the invention. However, upon desorption into the gas phase, the ejected ablation plume may comprise entrainment complexes that require further separation. To capture this ablated plume for further processing, a previously prepared substrate is placed in the path of the ejected plume, causing the plume to be deposited on the prepared substrates.

In a preferred embodiment, the prepared substrate comprises on or more wells having therein a substance for the separation of an analyte from a desorbed complex. In a non-limiting embodiment, the substance may comprise one or more denaturing agents (for example, methanol or surfactants) that assist in the unwinding and dissociation of protein complexes. After a predetermined incubation time for the dissociation of the captured complex, a second soft ablative desorption process is performed on the dissociated analyte, thus delivering the dissociated analyte into the gas phase. Accordingly, fully "naked" biomarkers are may be introduced to the gas phase intact using such an embodiment.

A preferred embodiment is illustrated in FIG. 8(a), where an initial soft ablative desorption step is used to propel the molecular complexes 600 intact without fragmentation onto a secondary target 505 (i.e. the prepared substrate). The sample may be in any initial form compatible with the soft ablative desorption method described above, for example, the sample may be a solid, liquid, or semi-solid. As disclosed above, soft ablative desorption is achieved using a first optical beam 515, preferably provided as a pulse 520, that is tuned to vibrationally excite a component within the sample 525. The sample is preferably provided on a substrate 530 transparent to the first optical beam to enable the positioning of the prepared substrate 505 close to the sample. In this example, the prepared substrate is shown as a sampling device comprising one or more wells, with each well containing a liquid 510 comprising a denaturing agent that dissociates the complex. The sampling device preferably comprises a device as disclosed in co-pending U.S. Provisional Patent Application Ser. No. 61/300,623, and more preferably is provided within the housing apparatus disclosed within the same. A multi-well sampling device is preferably as it affords rapid sampling and optionally provides spatially-resolved capture of the complexes. As such, the initial soft ablative desorption mechanism leads to lattice disintegration with all its constituent molecules propelled into the gas phase intact. This first step frees the molecules from the matrix and allows them to be exposed to new conditions, far from equilibrium, that lead to dissociation of complexes.

In FIG. 8(b), the prepared substrate, now containing the desorbed and dissociated complexes, provides a sampling device in which analyte molecules can be desorbed according to aforementioned embodiments of the invention. A second optical beam is directed onto a well 540 of the prepared substrate to ablatively desorb the now dissociated analyte within the liquid 510 contained in the well. The liquid 510 further comprises a component suitable as a propellant for soft ablative absorption—i.e. the component is characterized by vibrational levels to which the second optical beam is spectrally tuned (the component is preferably water). The ablative desorption process thus produces dissociated analyte 545. Subsequently, other wells may be processed simply by the relative translation of the prepared substrate relative to the second optical beam 535.

Thus, in a preferred embodiment of the present invention, highly associated biomolecules, or cellular matrix (membrane, endoplasmic reticulum) may be separated into their molecular constituents using a two step ablative desorption process, for applications in biodiagnostics of extracted bodily fluids.

In this procedure for biodiagnostics, the sample of bodily fluids may contain molecular species in complexes with multiple equilibria. Key molecular markers for disease states need to be isolated from complexes that would otherwise hide their identity. If the sample is compatible with direct exposure to a denaturant, then it may be initially prepared by dissolving it in a denaturant and spreading on a support substrate, as disclosed in the preceding embodiments involving a single ablative desorption step.

Figure 8:
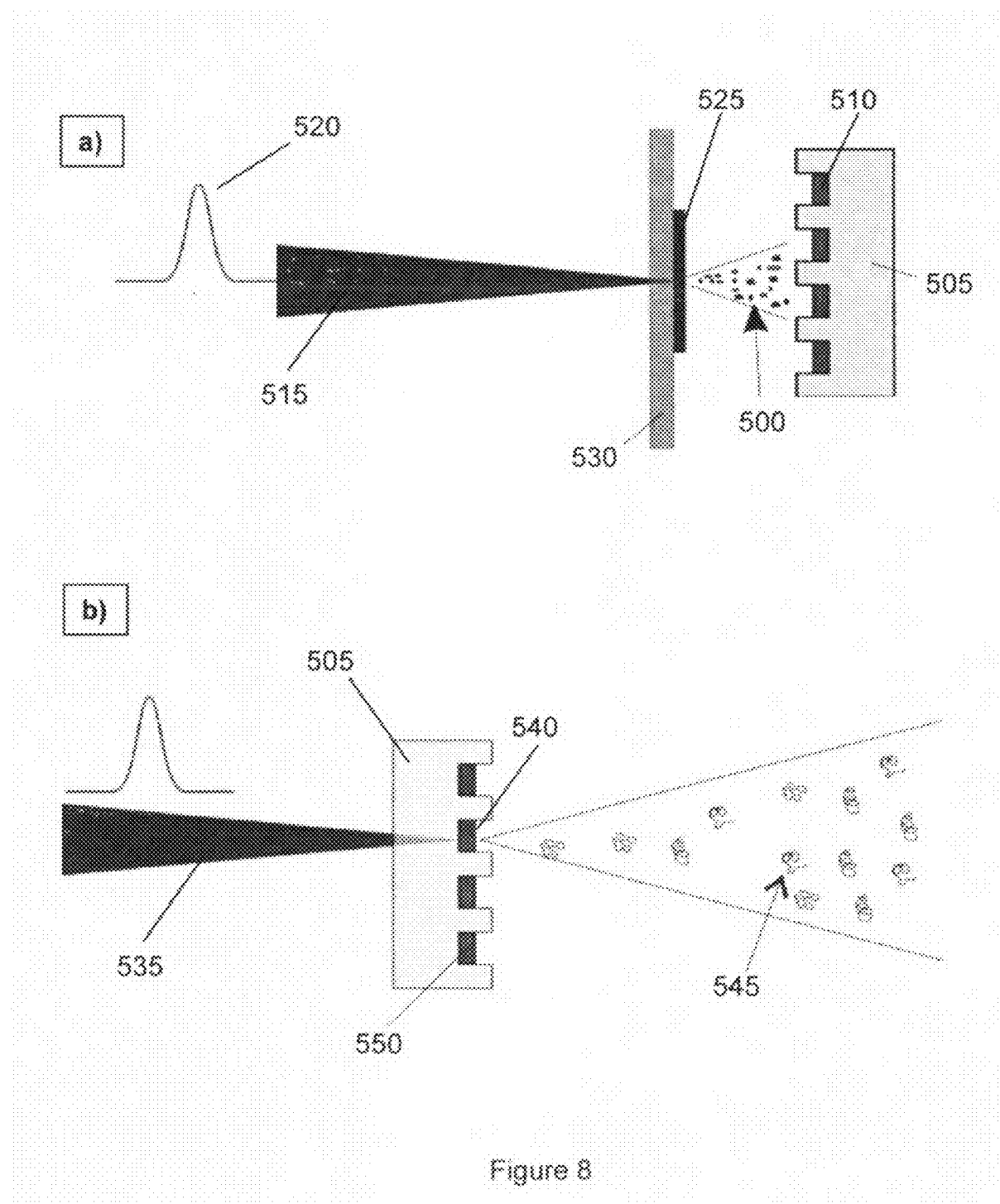
FIG. 8 illustrates a two-step ablative desorption process in which analyte is (a) first desorbed into an adjacent well containing a denaturant and (b) subsequently desorbed.

There are, however, a number of important examples such as bone tissue, soft tissue, and intracellular components in blood to name a few that require different pulse sequences but are still within the preceding embodiments of the invention, namely a single soft ablative desorption. Such molecular markers imbedded in these matrices (tissue/cells) are the most difficult cases to handle. In such instances, the two-step process shown in FIG. 8 is preferred to inject the biomarker into the gas phase with minimal fragmentation, followed by capture by a secondary medium that assists in disentangling complexes.

In a preferred embodiment of the invention, the preceding embodiment is adapted to provide spatial resolution capability. For example, if the wells of FIG. 8 have a diameter on the sub-micron scale, the method can be used to produce spatially resolved desorbed analyte within a single cell. This application is important for proteomics in terms of understanding gene networks and cell differentiation, particularly relevant to understanding cancerous states.

FIG. 9(a) shows a preferred embodiment in which the aforementioned two-step ablative desorption method is employed to make a molecular level map of the cell, which may be used to analyze and understand gene expression and regulation.

In one embodiment, a near-field optic may be used to selective desorb portions of a section of a cell onto a prepared substrate in the first step of the process. However, as illustrated in FIG. 9(a), the first optical beam provided for the first step of the two-step process need not be focused. The entire cell can be uniformly excited to ablate molecules into the gas phase.

Figure 9:
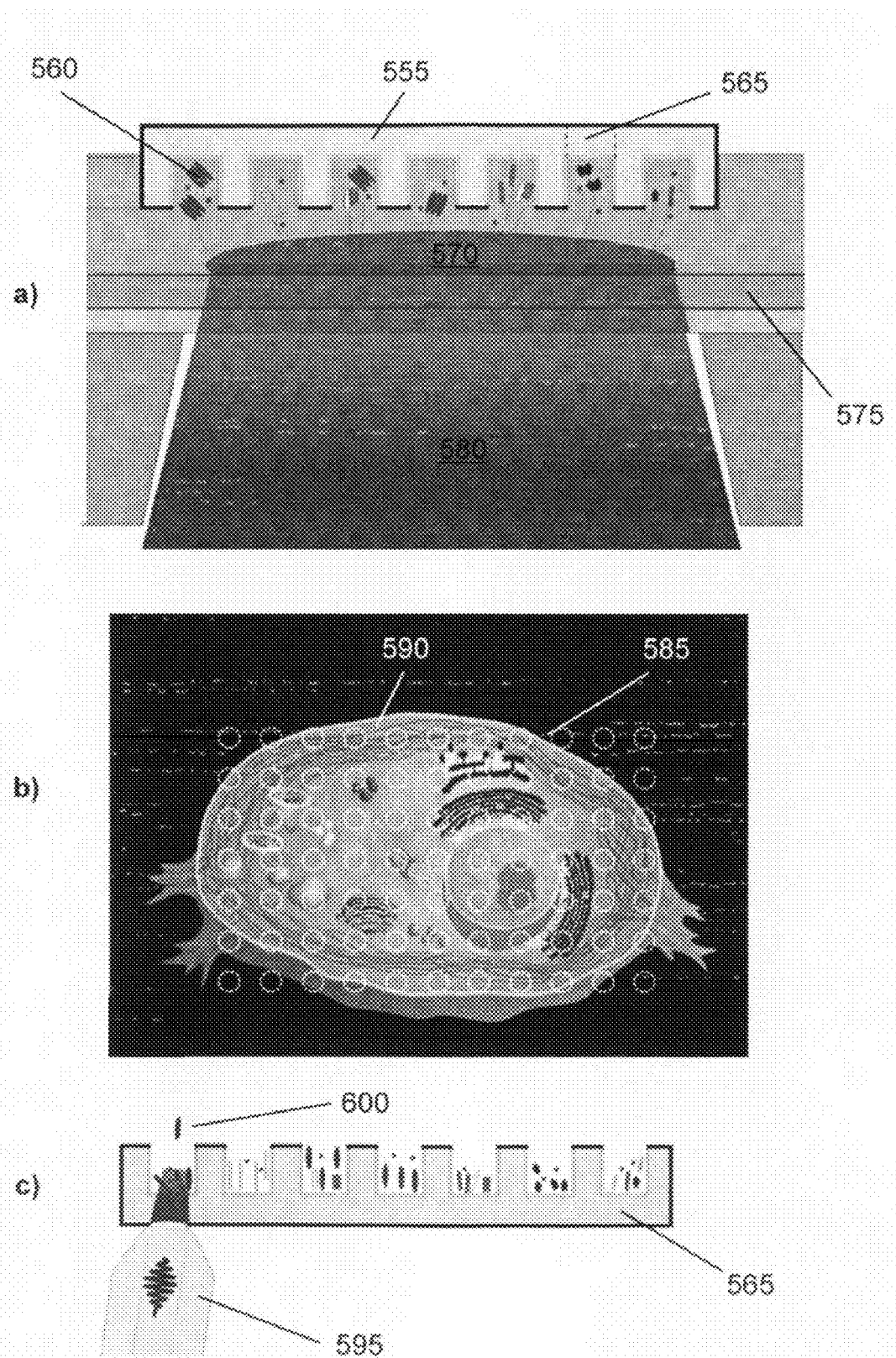
FIG. 9 shows an embodiment in which a sample is (a) initially ablatively desorbed into a spatial array of wells, as shown in (b), and (c) subsequently desorbed on a per-well basis.

Accordingly, in a preferred embodiment shown in FIG. 9(a), the prepared substrate 555 comprises a spatial array of wells 560. The well diameter 565 is preferably on the nanometer scale for the spatially resolved desorptive mapping of samples such as, but not limited to, biological samples and other samples having heterogeneity on the micron or submicron scale. During the initial ablative desorption step, a thin sample, such as a small cell or a thin section of a cell or other tissue 570, is supported on a substrate 575 transparent to the first optical beam 580. In the preferred but non-limiting embodiment shown in FIG. 9, the first optical beam irradiates the array of wells in parallel, thus desorbing the sample for the simultaneous and spatially resolved capture within the wells 560.

This procedure is similar to the two step ablation process shown in FIG. 8, but with the distinction of using smaller diameter wells 560 and spatial registration of the wells with respect to the coordinates of the sample (e.g. a cell or tissue section). For example, FIG. 9(b) provides an illustration overlaying the spatial positions of a well array 585 on a single cell 590. The diameter of the wells can be made as small as 10 nm by using current nanofabrication methods. The smaller the well size, the fewer different proteins and biomolecules contained within any given well. The wells preferably contain a denaturant and/or gel for separating molecules based on differential mobility.

As shown in FIG. 9(c), a second soft ablative desorption step is subsequently performed to desorb the dissociated analyte. However, in order to achieve spatial resolution on a single-well basis, the second optical beam irradiates each well separately. With sub-micron well diameters and spacings as disclosed above, this is preferably achieved using a near field optic 595. The desorbed analyte 600 may then be measured in an analytic method such as mass spectrometry, preferably using photo-ionization, as further discussed below. The quantitative, ultrasensitive, detection afforded by photo-ionization using either 1-photon threshold VUV photoionization or resonant multiphoton UV/Visible photoionization provides the molecular readout as a function of well position that in turn can be mapped onto the spatial position within the cell. In this manner, an entire molecular level map of the cell functions and expression can be made with 10-100 nm spatial resolution.

Embodiments of the invention disclosed above provide methods for the soft desorption of analyte from a wide variety of samples, where the analyte is desorbed into a gas phase in the form of an ablation plume ejected from the sample following optical irradiation. As noted above, the unique desorption method of the preceding embodiments yields desorbed analyte that is substantially unfragmented, has very low energy relative to the hot component acting as the ablative propellant, and is desorbed substantially in its native charged state without further ionization. These features stand in stark contrast to all prior art methods of desorption and sample preparation.

As noted above, the soft desorbed analyte present in the ablation plume produced according to any one of, or combination of, the preceding embodiments, may be further analyzed by one of many methods that can probe gas phase species, including, but not limited to, mass spectrometry, creating supersonic molecular beams, ultrafast electron diffraction, any gas phase spectroscopic methods. When coupled with mass spectrometry, the soft ablative desorption method allows for the sensitive detection of biomarkers and other analytes. The soft ablative method enables quantitative analysis of the material composition as the molecules enter the gas phase intact without undergoing fragmentation.

Figure 10:
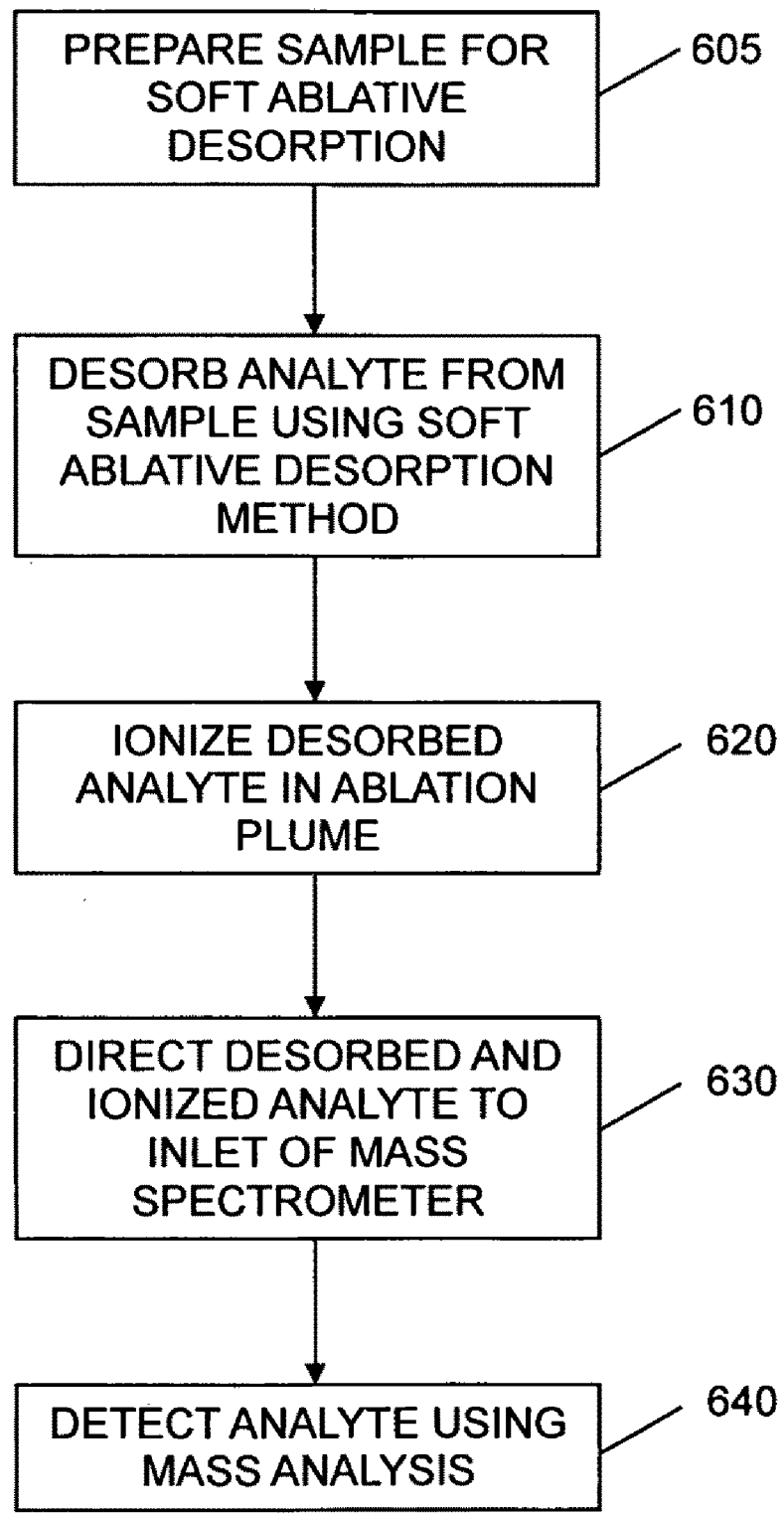
FIG. 10 provides a flow chart illustrating a method of performing the ablative desorption process.

Therefore, a preferred embodiment of the invention, as illustrated in the flow chart shown in FIG. 10, provides a method of detecting an analyte by mass analysis. The sample is first prepared for soft ablative desorption in step 605, preferably by providing a sample having a thickness on the order of the absorption depth of the irradiating optical beam. In step 610, the analyte is first desorbed from a sample using the soft ablative desorption method described above. Subsequently, in step 620, the ejected plume containing desorbed analyte is ionized. In step 630, the ionized analyte is directed to the inlet of a mass analysis device that preferably comprises a mass spectrometer. Finally, in step 640, the analyte is detected by mass analysis.

In addition to the criteria for ablative desorption of the analyte, in a preferred embodiment of the invention, the optical beam is delivered on a sufficiently short timescale to enable the ablative desorption process to occur on timescales faster than even energy transfer from the hot component acting as a propellant to the desorbed analyte. In many analysis methods, including mass spectrometry, it is important to have molecules enter the gas phase with as little excess energy as possible to prevent excessive fragmentation and loss of identity in the detection process through multiple thermal fragmentation pathways. For example, in the case of mass analysis highly purified protein samples, fragmentation is not a problem, as long as there is as detectable parent ion, and one is dealing with a single molecular species. The problem is really when one is dealing with mixtures, such as direct analysis of body fluids or tissues, when overlapping fragmentation patterns will mask the identities of the molecules of interest. In the publication, R. J. Dwayne Miller, "Vibrational-Energy Relaxation and Structural Dynamics of Heme-Proteins," *Ann. Rev. Phys. Chem.* 1991, 42, 581-614, the present inventor was the first to characterize energy relaxation pathways in biological molecules. It typically takes several tens of picoseconds for energy to be dissipated from an excited protein molecule to the surrounding water molecules. The process is microscopically reversible through collisional exchange. As such, the work reviewed in this reference demonstrates it takes on the order of 10 to 100 picosecond time scales for significant amounts of energy to be transferred from highly excited water molecules into a protein.

The aforementioned 10 ps timescale pertains to relatively small amounts of energy exchanged between water and the protein. The time scale becomes significantly longer as the amount of excess energy involved increases. Basically many more collisions of the water are required to transfer energy to the biomolecules. Each collision can only deposit about 10 $cm^{-1}$ of excess energy from the hot water molecules to the protein. So for the superheated conditions involved in ablation, the time scale for significant transfer of energy from the highly excited water to the target protein or other molecules of interest can take times up to 100 ps and longer. This time scale is longer than the ablation process itself, using water as the propellant, such that the molecules of interest can be introduced into the gas phase as cold as possible. Again, this feature relating to an aspect of the invention is highly desirable as it is preferably for molecules to enter the gas phase with as little excess energy as possible to prevent excessive thermal fragmentation for the most exacting identification of the molecular species of interest. As noted above, this condition is met for aqueous samples by using infrared laser pulses tuned to specific molecular vibrations of water that have pulse durations of less than 1 ns, and ideally less than 100 ps.

A wide range of ionization methods may be used to ionize the desorbed analyte prior to mass analysis, including conventional ionization mechanism such as electrospray ionization, coronal discharge, chemical ionization and thermal emission, fast atom bombardment, photoionization, inductively coupled plasma ionization, and other plasma based methods of ionization such but not limited to as direct analysis in real time (DART).

Figure 11:
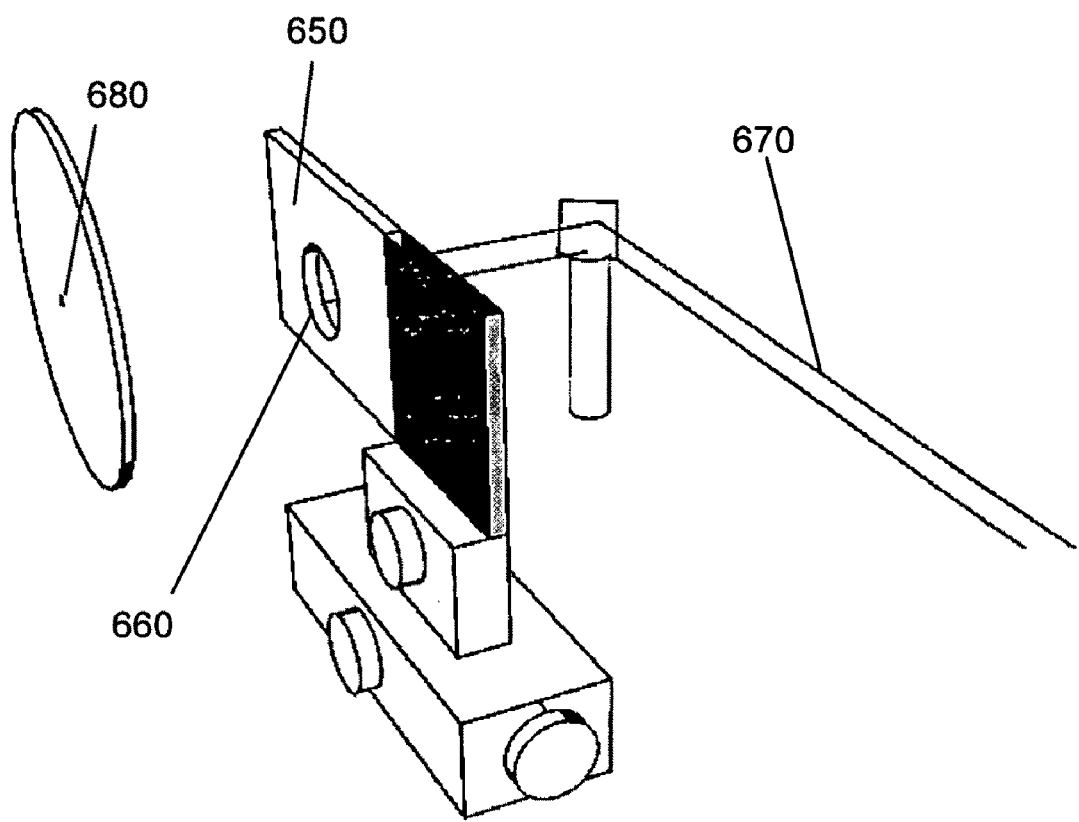
FIG. 11 shows a schematic of a system in which a sample holder is positioned adjacent to an inlet of a mass spectrometer.

FIG. 11 illustrates a preferred embodiment of the invention in which a thin sample having a thickness on the order of the absorption depth of the optical beam is provided on a sample holder 650, preferably comprising a well 660. The sample holder is preferably transparent to the optical beam employed for soft ablative desorption, enabling the beam to be directed onto the sample from the back side. Alternatively, the optical beam may be directed onto the top surface of the sample at an angle. As described above, the use of a sample with a thickness on the order of the absorption depth of the optical beam is preferable as it substantially reduces or eliminates the effects of recoil, which can otherwise interfere with the subsequent mass analysis step.

The sample holder 650 is preferably mounted on system that enables relative translation, such as a multi-axis translation stage 690. The sample holder may house the sample in many forms, including a thin layer of solid or semi-solid sample, or one or more wells for providing a thin layer of liquid sample. As noted above, preferably sample holder embodiments for use with soft ablative desorption and mass spectrometric analysis are disclosed in co-pending U.S. Provisional Patent Application Ser. No. 61/300,623. For the case of liquid samples, the sample holder preferably comprises one or more wells contained within a housing apparatus as disclosed in Provisional Patent Application Ser. No. 61/300, 623, as described above. In a more preferable embodiment, the sample holder apparatus is also transparent to the optical beam, enabling the optical beam to be provided through the rear of the housing apparatus and the sample holder, whereby the desorbed analyte may be ejected through the aperture in the housing. Beam path 680 preferably includes mirror 685 for directing the optical beam onto the sample at normal incidence. Beam path 680 may further comprise additional optical elements, such as a beam shaping optic for providing a substantially-flat top optical beam.

The optical beam is first directed onto the sample, producing soft ablative desorption of the sample. After a prescribed time delay, the ablated plume is ionized, preferably using a photoionization beam (not shown) as described below. The ionization beam preferably produces photo-generated ions in the ablation plume using threshold ionization. Accordingly, the ionization beam is preferably a vacuum ultraviolet (VUV) beam. In a first non-limiting embodiment, the VUV beam may be generated from laser harmonics (for example, using methods disclosed in Eden, J. G. Progress in Quantum Electronics 2004, 28, 197-246).

In a preferred embodiment, the VUV pulse tuned to the threshold for ionization for the analyte of interest to deposit the least amount of excess energy as possible into the ion formation process to maintain the narrowest possible molecular fragmentation pattern. Preferably, the excess ionization energy is less than about 1 eV. The wavelength of the ionization pulse is preferably in the 7-10 electron Volt (eV) or 100-200 nm wavelength range for many biomolecular analytes. In one embodiment, the VUV wavelength may be tuned to exploit threshold ionization of specific analytes of interest as an optical filter.

The time delay between the first optical beam driving ablative desorption and the VUV pulse used for quantitative ion generation is preferably set between 1 nanosecond to 1 millisecond, depending on the spatial location of the VUV beam with respect to intercepting the ablation plume in order to generate ions as needed for mass spectrometry detection. Here, it should be mentioned that the time interval between the optical beam used for ablation and the VUV beam for ionization is typically quite long due to the relatively slow speed of the molecules in the gas phase and spatial dimensions associated with ion collection. The ionization process depends solely on the energy of the VUV beam such that either single pulses or trains of pulses can be used, as is most practical for delivering the required energy for maximal ion generation.

Since the absorption of VUV depends on the molecular cross section for absorption, the ion generation step is fully deterministic, reproducible, and thus enables quantitative mass spectroscopic determination of the molecular species. By using high enough energy laser pulses, this absorption process can achieve close to 100% efficiency with respect to ion generation. For example, if the molecular absorption cross section is $10^{-15}$ cm$^2$, a typical cross section for resonant VUV transitions, then a laser beam with $10^{15}$ photons/cm$^2$ will excite 67% of the molecules its path.

In a preferred embodiment, laser pulses with $10^{16}$ photons/cm$^2$, or approximately 1 microjoule for a 100 micron focus, are employed and it is possible to effectively excite substantially all of molecules within the laser beam path. This level of VUV generation is well within recent advances in laser technology. As ion collection optics can achieve 100% collection efficiency for charged particles, this embodiment of the invention provides a prescription by which mass spectrometry can achieve very sensitive detection, potentially at the single molecule level.

The above embodiment in which two pulses are provided, one for driving ablation and one (or series of pulses) in the VUV to photogenerate ions preferably used for samples that consist of homogeneous molecules of interest and are free from aggregates. In proteomics applications and biodiagnostics involving tissues or whole cells, the sample may be heterogeneous and the molecules of interest exist in complexes. For this class of samples, an additional pulse may be required such that the laser pulse sequence consists of 3 pulses, namely two pulses for dissociation and ablative desorption and one VUV pulse for photoionization. The first optical pulse in this scenario is used to excite as small a volume as possible of the sample to limit the number of molecules ejected into the gas phase. The molecules that are ablated are captured on a secondary medium that leads to new equilibrium conditions in which the molecular, complexes dissociate to individual molecules. The second IR laser pulse will be tuned to the vibrational spectrum of a particular molecular component of this secondary medium, typically the bulk component comprising the lattice, to drive ablation of the now isolated molecules into the gas phase. The third laser pulse is the VUV pulse (or train of ionizing pulses) as before and its role is to ionize the molecules of interest in a quantitative fashion, as described above.

The sample holder is preferably positioned to orient the sample immediately below a small aperture that allows the desorbed and photo-ionized molecules to enter into the mass spectrometer and encounter as little intervening air molecules as possible to avoid collisional cooling and cluster formation, droplet formation, and shock wave propagation from compressed air from the ablation blast (as further discussed below). The use of an aperture is a typical procedure for environmental cells adapted for water samples but employing differential pumping to create high vacuum conditions above the sample. By making this distance above the sample as small as possible (preferably about 100 microns above a 100 micron pinhole) the problem of interactions with ambient air is substantially reduced.

Another important reason for including a differentially-pumped zone about the sample is that the VUV pulses for the photogeneration of ions as described above require the ablation plume to travel into an evacuated region to avoid VUV light absorption by the air, attenuation of the VUV pulse, and generation of unwanted ions. This latter condition is satisfied by the above sample holder considerations.

Figure 12:
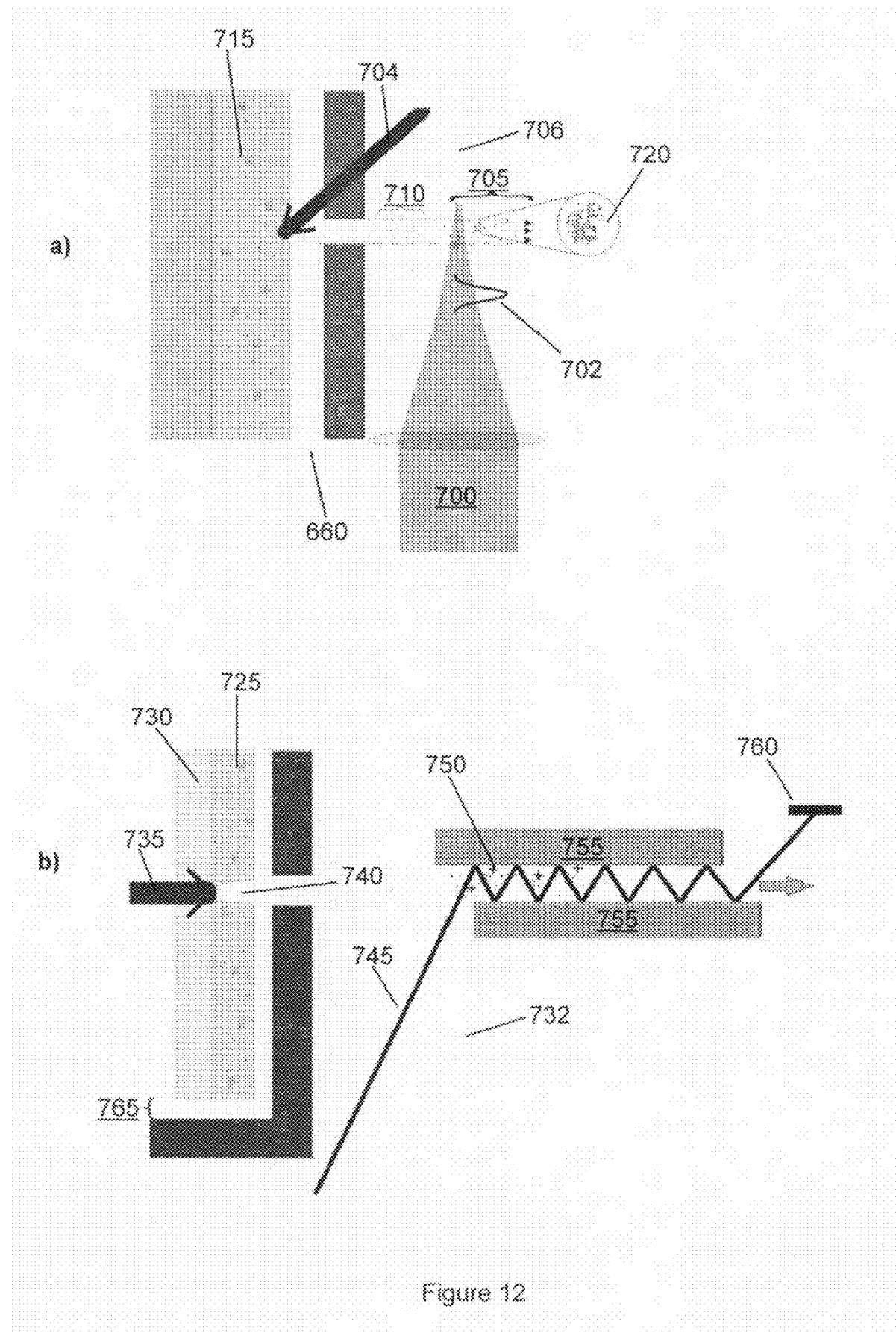
FIG. 12 illustrates the photo-ionization of a sample by a vacuum-ultraviolet beam for (a) an optically thick sample and (b) and optically thin sample.

FIG. 12 illustrates the multiplexing of a photo-ionization VUV beam with the soft ablative desorption optical beam for quantitative mass spectrometry and molecular identification for thin and thick samples. These figures show schematically a VUV laser pulse intersecting the ablated plume within an evacuated region. The evacuated region is preferably within the mass spectrometer. This interaction needs to occur in a substantially evacuated zone above the sample to avoid absorption of the VUV by air. This is preferably accomplished by placing a differentially pumped aperture above the sample. The region between the sample and aperture is preferably maintained at approximately 5 torr, which is the about the vapour pressure of water at room temperature. Preferably, the region between the aperture and the ion collection optics is at high vacuum, pressures of less than $10^{-6}$ torr being typical.

More specifically, FIG. 12(a) shows an optically thick sample 715 where there is secondary mass ejection and droplet formation due to recoil effects, as discussed above. The VUV ionization beam 700, preferably an optical pulse 702, is timed to overlap with the front edge of the ablation plume 705 within a vacuum region 706 where the molecules have undergone ablative desorption by the optical beam 704 and are free of droplet formation (note the presence of droplets 710 following the ablation plume 705). The VUV beam is focused down to the dimensions of a few microns to spatially match this preferred interaction zone, producing ionized analyte 720 that is further directed towards the mass spectrometer inlet.

FIG. 12(b) shows an optically thin sample 725 provided on a substrate 730 that is transparent to the optical beam 735. In this example, the irradiated zone of the sample disintegrates and all molecules are ejected into the gas phase without the presence of droplets. The timing of the VUV ionization beam 745 is less critical in this case, and the beams do not need to be focused other than to match the cylindrical volume element of the ablation plume 750. In a preferred embodiment, a multipass arrangement is employed, as shown by VUV reflecting mirrors 755, to increase the absorption efficiency and ion generation. The VUV beam, provided within vacuum region 732, is interrupted after ionizing the ablation plume by beam dump 760. As in FIG. 12(a), the intermediate region 765 is differentially pumped to maintain a low vapor pressure.

Due to the orientation of the sample holder, in which the surface normal passing through the irradiated zone within the sample is oriented towards the inlet of a mass spectrometer, the ionized analyte within the ablation plume is further transported through the inlet and into the mass spectrometer. Optionally, additional focusing elements such ion funnels and other means of ion guiding using either DC or RF voltages, as known in the art, may be provided to further focus the ionized sample to the inlet of the mass spectrometer.

Figure 13:
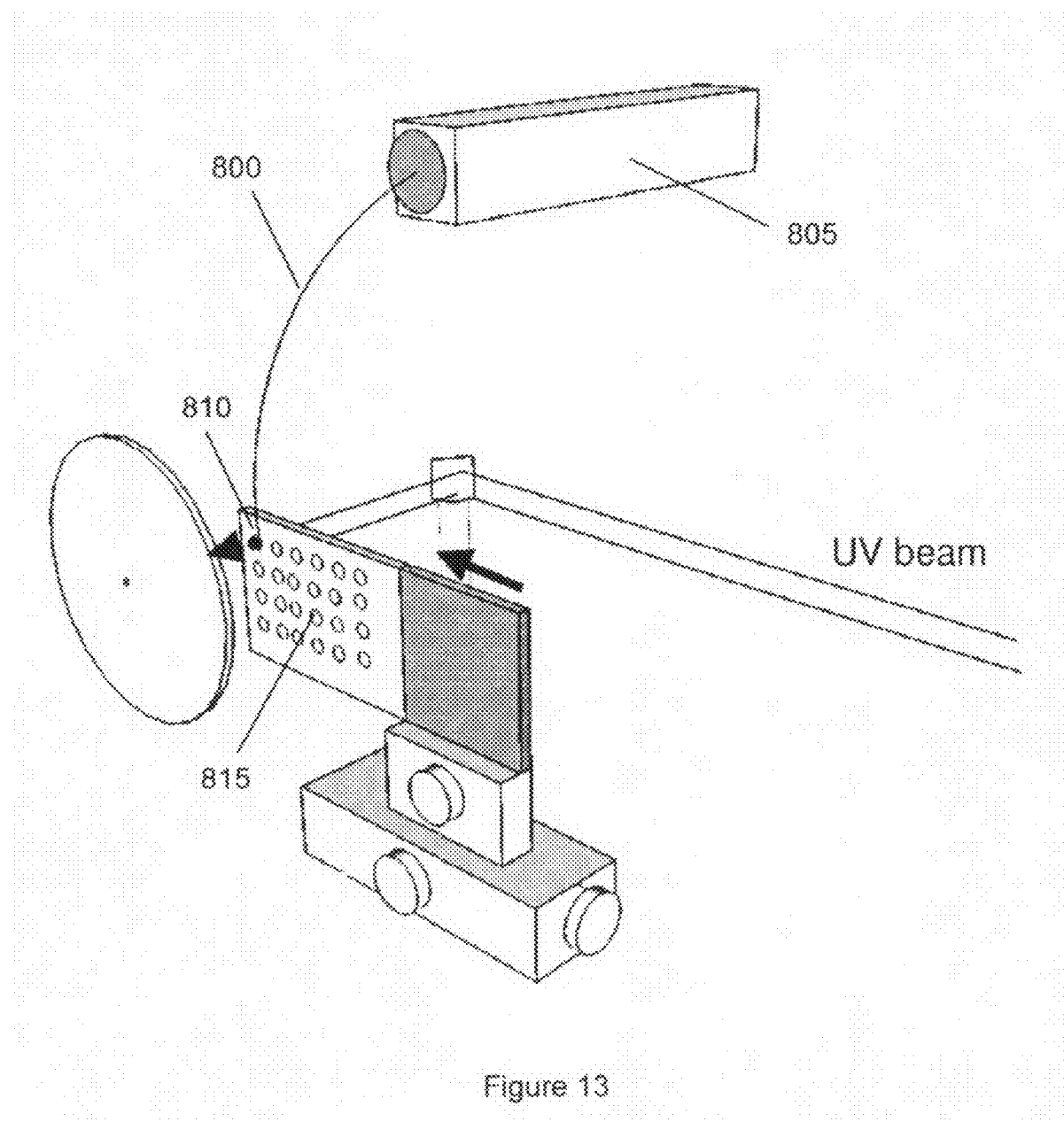
FIG. 13 illustrates a system where an array of wells are filled using a capillary device prior to ablative desorption and subsequent detection by a mass spectrometer.

FIG. 13 provides a related embodiment in which the sample holder comprises a planar array of microwells 815 that are filled by a capillary 800 from a capillary electrophoresis system 805 or a system for flowing a sample liquid in a capillary such as a flow pump. This embodiment combines the separation efficiency of capillary electrophoresis with the efficiency, reproducibility and quantitative nature of mass spectrometric analysis based on soft ablative desorption. As described above and in co-pending U.S. Provisional Patent Application Ser. No. 61/300,623, a well is filled by forming a droplet or a portion of a droplet at a distal end of the capillary and contacting the droplet with the well. Preferably, the well is adapted to be filled by a dynamic wetting process in which the contact of a droplet residing on the surface of a substrate with the top of a well results in the filling of the well with a stable and thin sample volume. Accordingly, the multiple wells in the well array may be serially filled by contacting on the tip of a capillary with a first well, filling the well, replenishing the droplet (either passively or with an active means such as a pump), and subsequently contacting the replenished droplet with an additional well. This process may be repeated to fill an array of wells and correlate each sample aliquot with an position or time for separation analysis. In another embodiment, the capillary may comprise a fingerstick capillary for directly providing capillary blood to a sampling device for analysis.

Figure 14:
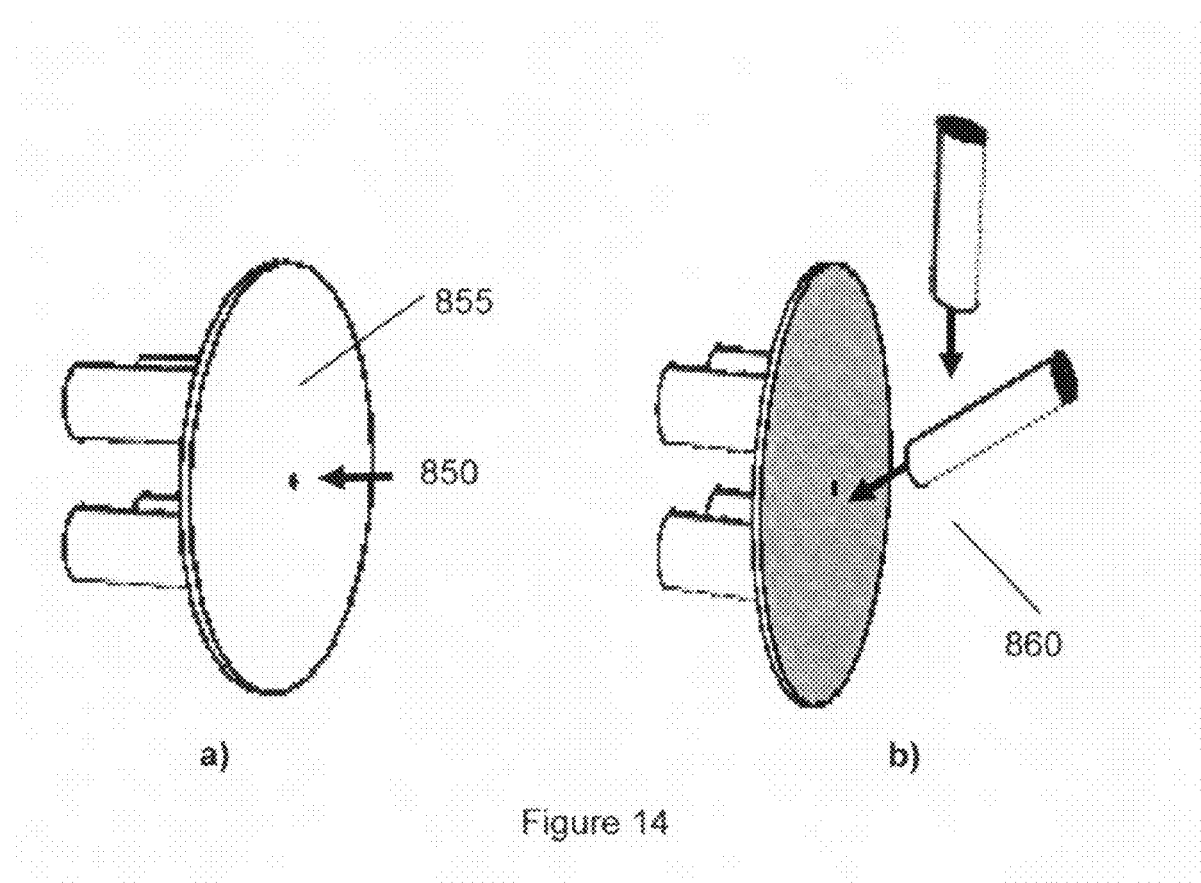
FIG. 14 compares the injection of sample into a mass spectrometer according to (a) an embodiment of the present invention and (b) an electrospray injection process.

The direct ablative desorption and photo-ionization is beneficial for low-noise mass spectral analysis, as evidenced by FIG. 14, which compares the efficiency of ion injection for (a) an embodiment of the present invention and (b) an electrospray ionization system as known in the art. In FIG. 14(a), the ionized ablation plume is directly transported through the inlet aperture 850 of mass spectrometer 855. This geometry, where the sample holder, and hence the ablation plume both posses an axial symmetry with the ion optics inside the MS device, results in a more efficient method of ion collection than prior art methods as shown in FIG. 14(b).

The aforementioned embodiments enable quantitative mass spectroscopy with several orders of magnitude increase on the efficiency of ion generation. This procedure can be applied to all present methods of mass spectrometry to attain corresponding increases in sensitivity and throughput that comes with increased sensitivity. Non-limiting examples of mass spectrometry systems that may be used for the subsequent mass analysis of desorbed and ionized analyte include sector, ion trap, quadrupole, and time-of-flight systems, and combinations thereof.

In yet another embodiment, sequential resonant two-photon absorption may be employed for photo-ionization. Preferably, an optical beam may be provided with a wavelength in the 200-300 nm range to attain ionization. In a preferred embodiment, the ground state to excited state is driven to saturation, whereby the second pulse ionizes the analyte in the linear regime. Such an embodiment is preferable in that simpler and more cost effective laser sources may be utilized.

Figure 15:
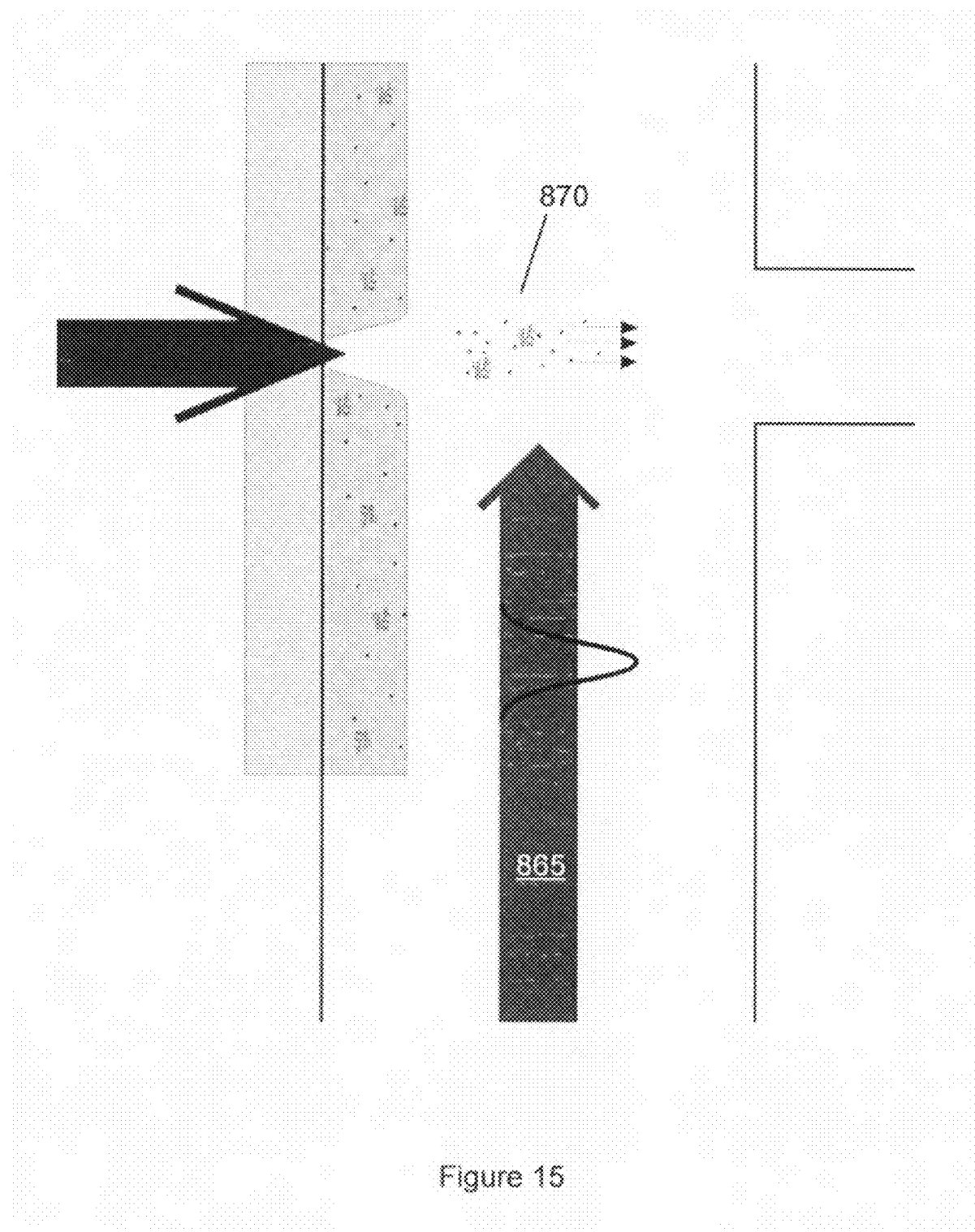
FIG. 15 illustrates the photo-ionization of an ejected ablation plume using linear resonant excitation under ambient conditions.

FIG. 15 shows an alternative photo-ionization embodiment to the aforementioned VUV approach, in which the ionization beam 865 used to quantitatively generate ions within the ablation plume 870 is not in the VUV spectral region. The photoionization step can be implemented under ambient conditions which is important in many applications. The photoionization step is conducted in all cases using all resonant 1-photon processes, under saturated conditions, to enable quantitative ionization of nearly all molecular species in the beam path.

Figure 16:
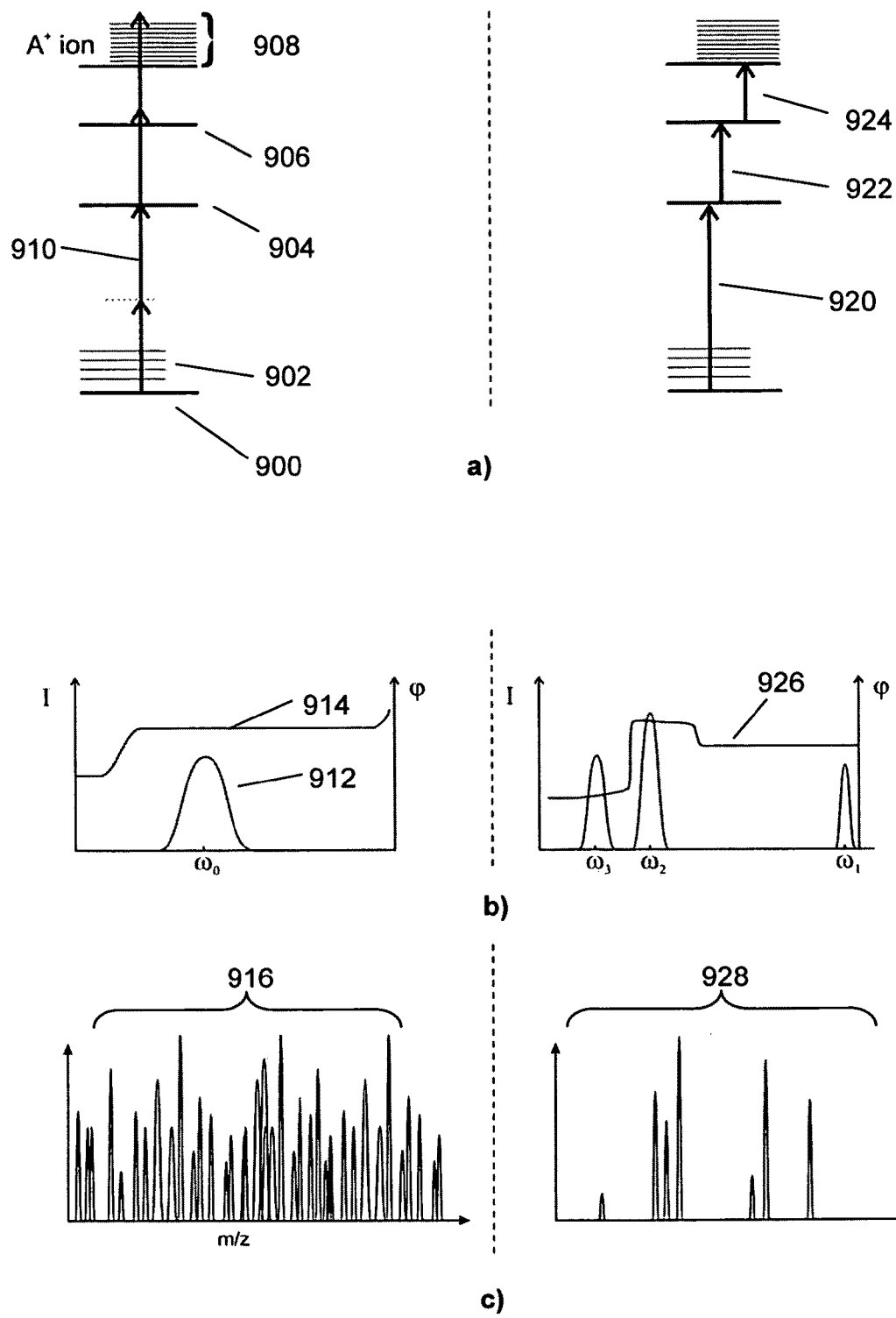
FIG. 16 illustrates the linear resonant photo-ionization process, showing (a) energy levels of a molecule, (b) the spectral content of a photo-ionization beam, and (c) a resulting mass spectrum.

This is preferably achieved using an optical chromatography method, as illustrated in FIG. 16. The figure shows an energy level diagram for an excited molecule, comprising a first electronic state 900, vibrational levels 902, a series of excited electronic levels 904 and 906, and ionized state 908, above which excess deposited energy produces fragmentation. The left side shows the effect of indiscriminant ionization using nonresonant multiphoton ionization, where each photon is represented by vector 910.

The corresponding pulse typically used in this case is what is referred to as a transform limited pulse. This pulse shape is given in the figure below (left middle panel). The spectral pulse 912 is centred at a central wavelength, $\omega_0$, and the phase $\phi$914 is the same for all wavelengths within the bandwidth of the pulse. This gives the shortest pulse for a given bandwidth. Such a pulse leads to indiscriminate multiphoton ionization, as there is no time ordering of what electronic levels are addressed by the laser field. The molecular ion is prepared with a wide distribution of possible states with varying degrees of excess energy.

This effect leads to a broad distribution of molecular fragments as shown schematically in the lower left panel. This wide distribution of fragments 916 makes identification of the molecule, especially within a mixture, difficult. The peaks from different molecules overlap and there is not a unique signature for the molecule of interest.

The right hand side of FIG. 16 shows, in contrast, the control one can achieve with fully resonant 1-photon processes to ionize the molecule. Each molecule has a distinct electronic spectra and power spectrum for any ensuing fragmentation pattern. By matching the laser excitation spectrum to the molecular spectrum using 1-photon absorption 920, 922 and 924, a unique, relatively narrow fragmentation pattern can be achieved to help identify the molecular species (bottom right panel).

The pulse in this case has a structured phase profile 926 that exposes the molecules to a field at a given frequency $\omega_1$, then $\omega_2$, and finally $\omega_3$ to selectively ionize the molecule at threshold to give a narrow distinctive molecular signature 928.

The degree of selective ionization and separation of molecular species in the ionization step (optical chromatography) is shown in FIG. 16. Each transition that is resonantly enhanced, by matching the frequency of the applied field to the energy separation between electronic states, leads to a factor of 10-100 enhancement. Since the overall ionization involves multiple transitions, resonantly matched ionization can give selectivity in excess of 10,000 in terms of identifying one species A from a mixture of ABC as shown schematically in the figure. More specifically, the energy levels of molecule B, shown at 930, and molecule C, shown at 932, are non-resonant with the spectral content of the optical pulse train shown by vectors 936, 938 and 940. Molecule A, on the other hand, is has an energy level structure 934 that is resonant with the optical pulse train, leading to selective ionization with low background from molecular species B and C.

Accordingly, in a preferred embodiment, the optical ionizing beam may comprise a temporal sequence of 1-photon resonant visible and UV pulses appropriately timed to terminate at the same threshold ionization state to minimize fragmentation and loss of molecular identification. It is recognized in this invention that ionized molecules by such a deterministic process will give characteristic fragmentation patterns that assist in molecular identification. The particular spectrum of UV to VUV components to the pulse can be used to explicitly generate particular fragmentation patterns that are highly molecular specific.

With respect to implementation of the present invention, one trained in the art of ultrafast lasers can achieve the VUV wavelengths for photoionization, for example, by using high harmonic generation of commercially available lasers or using combinations of 1-photon resonant processes to reach the same ionization threshold. The latter process of multiphoton resonance makes it possible for low cost lasers and offers a further degree of selectively in the photoionization process as additional contrast in the detection step using mass spectrometry.

Even higher selectivity for ionizing a particular molecule can be achieved through the use of shaped, ultrashort pulses. Using Spatial Light Modulators (or Liquid-Crystal Mask, MEMS or Acousto-optic Modulators) for example, it is possible to shape the phase and spectrum of ultrashort pulses in order to maximize the ionization efficiency of a target molecule. Because the phase and spectral profiles of the optimal pulses depend intimately on the particular quantum states of the target molecule, such ionization is ideal for particular molecule while not necessarily very effective for other molecules, thereby enhancing considerably the selectivity of the measure.

This aspect of the invention gives a prescription for highly efficient ion generation without fragmentation of the analyte molecule of interest and simultaneously provides additional selectivity by exploiting optical fingerprints of the electronic spectra of molecules. Direct optical ionization from soft ablatively desorbed neutral molecules, according to preferred embodiments of the invention, therefore provides an inventive and highly useful alternative to MALDI and electrospray methods known in the art.

Since the absorption of light is linear this process is completely deterministic. An important feature of this preferred embodiment of the invention in this regard is that it provides a prescription for achieving the light fields to achieve substantially reproducible and highly efficient, ion generation, a prescription that is made possible by the aforementioned embodiments of the invention involving soft ablative desorption of analyte from a sample. Moreover, the use of soft ablative desorption to provide substantially unfragmented and non-ionized analyte molecules in the gas phase makes the application of this ionization mechanism possible for even very large molecules that otherwise have negligible vapour pressure.

This unique feature of the soft ablative desorption and resonant linear photo-ionization process that provides deterministic ion generation for quantitative mass spectroscopic analysis can be clearly contrasted with inefficient prior art methods involving the simultaneous desorption and ionization of analyte that may lead to a fragmentation of analytes of interest. Unlike embodiments of the present invention, the environments created by MALDI or electrospray ionization create ions as part the mechanism ejecting molecules into the gas phase. In this regard, photogeneration of ions only adds to the nonlinear ion densities. Direct photoionization cannot overcome the inherently nonlinear ionization process in the MALDI and electrospray methods of volatilizing molecules themselves. It is only in the event that one has molecules injected into the gas phase intact will photogeneration of ions lead to reproducible results. Accordingly this unique combination of soft ablative desorption and resonant linear photoionization together that imparts truly quantitative capabilities to mass spectrometry.

As noted above, this embodiment of the invention employs resonant linear photoionization of the molecules of interest to provide the charged particles for mass spectroscopic determination of the molecular identity. The fact that the ablative desorption process occurs on a picosecond to nanosecond time scale, as a pulsed burst of gas phase molecules, enables the use of time multiplexing additional laser pulses for enhanced detection using mass spectrometry.

An important feature of photoionization with respect to the present embodiment is that the ion generation step is determined by the absorption cross section of the molecule and that this cross section is molecule specific. This feature of the ionization step is determined by the absorption cross section for light at wavelengths shorter than the ionization threshold (photon energies in excess of the binding energy of the electron to the molecule) and makes the process substantially deterministic and quantitative with respect to ion generation for detection and identification using mass spectrometry.

Aspects of the present invention thus address a key problem in the use of mass spectrometry for ultrasensitive molecular detection. In principle, mass spectrometers can detect single molecules. Once an ion is generated there are well established methods to detect ions using ion optics to selectively focus the ion to a detector. This single molecule detection limit is a key limit to mass spectrometry and other analytical methods. Mass spectrometry approaches this limit due to the charged nature of the particle detection process.

This limit has not been attained prior to this invention as prior art methods for volatilizing the molecules and subsequent ionization mechanisms are inefficient, nonlinear, and not reproducible to the degree required for quantitative analysis. In particular, prior art methods of volatilization and ionization of samples for mass spectrometry are often unsuitable for clinical diagnostics where high accuracy and precision is essential. The conventional mechanisms for ion generation based on MALDI only produce about 1 ion out of $10^4$ molecules (Mass Spectrometry Reviews, 1998, 17, 337-366). Therefore, even if the method itself was intrinsically capable of detecting single (charged) molecules, it has not been possible to generated ions efficiently or reproducibly enough to achieve this limit. In contrast, in the limit of saturated absorption of the incident beam, it is possible to photo-ionize all the molecules in the laser path. Thus, embodiments of this invention can increase the sensitivity of mass spectrometry by a significant factor.

Equally important for achieving significantly improved sensitivity is the deterministic and repeatable nature of the desorption and ionization processes according to embodiments of the invention. Such repeatability is important for achieving measurements with good precision and a low limit of detection. Accordingly, embodiments of the invention can be employed to attain highly sensitive detection capabilities with quantitative accuracy, with applications in the detection of biological markers at early stages of a disease from a small volume of sample.

For optimal detection sensitivity, the second pulse, in the simplest two pulse case, is suitably delayed in time for the action of the ablative pulse to enable the molecules to fully enter the gas phase and enable clusters of molecules to dissociate as fully as possible.

A more general embodiment of the invention involves a series of pulses spanning the IR to VUV range to maximize efficiency in the overall generation of ions of the particular molecule of interest. There is an initial sequence of short IR laser pulses tuned to various molecular vibrations that serve to ablate the molecules into the gas phase using soft ablative desorption, and to untangle molecular complexes by giving them enough energy to overcome barriers to dissociation into individual molecules. These IR laser pulses and timing are adjusted to optimally propel isolated molecules into the gas phase intact. Similarly, the pulse sequence for photogeneration of ions can be generalized to a series of pulses tuned to specific electronic resonances of the molecule. Each molecule has a unique electronic signature. By using a sequence of visible to UV pulses, as apposed to direct VUV ionization, it is possible to both match the laser spectrum to the molecule of interest to achieve deterministic ion generation and control the fragmentation pattern in a known way that enables one molecule to be isolated from others in a form of optical chromatography.

In all cases, the above time and wavelength multiplexing of IR, visible, UV, to VUV laser pulses leads to quantitative ion detection through the unique use of soft ablative desorption to propel molecules into the gas phase with the minimal excess energy possible—substantially free of thermally generated ions and/or excessive fragmentation.

As noted above, in a preferred embodiment, the sample desorption process is performed as a two-step process in which spatially resolved portions of the sample are first desorbed and captured onto a prepared substrate comprising an array of wells containing a liquid comprising a denaturant. The use of spatially separated wells also enables spatial resolution in the ablative desorption process and makes it possible to use analytical methods such as mass spectrometry for mapping, quantitatively, the specific composition of a material as a function of position. This simple approach enables spatial resolution down to and beyond 100 nm resolution, depending on the well diameter and spacing.

This feature alone is unique and far superior to the use of ion milling methods to provide mass spectrometers with spatial resolution. See for example the paper of C. G. Marxer et al, entitled "Supported membrane composition analysis by secondary ion mass spectrometry with high lateral resolution" BIOPHYSICAL JOURNAL Volume: 88 Issue: 4 Pages: 2965-2975. The use of ion milling leads to complete disintegration of the molecules of interest and one only obtains atomic composition not molecular composition. In order to obtain any quantitative information using ion milling, one needs to use isotopically labeled molecules and compare ion fragment ratios, a complex and laborious procedure. The spatial resolution feature according to the present embodiment is especially useful in proteomics research, as it provides a tool to construct a chemical map of the workings of a cell.

Figure 18:
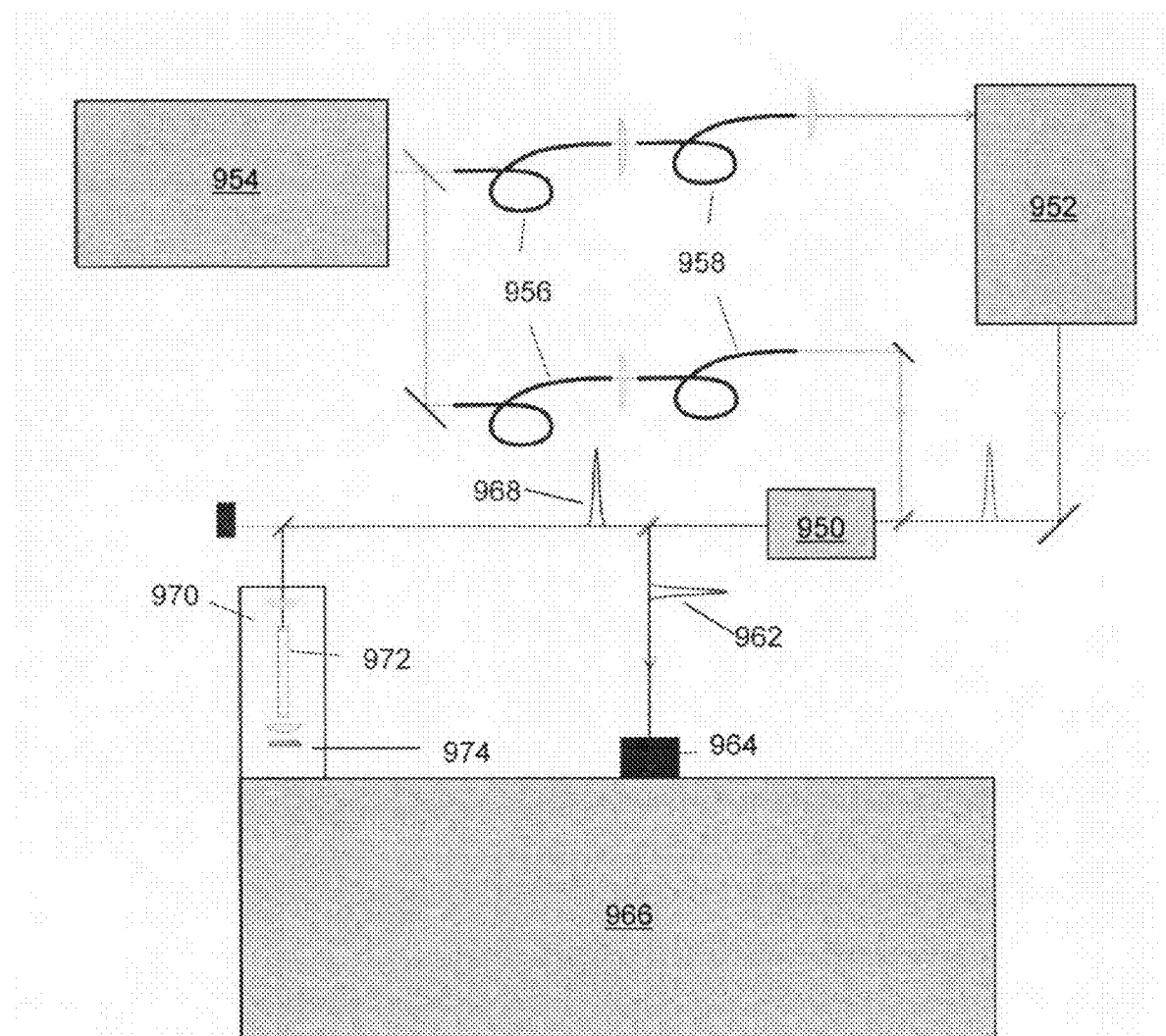
FIG. 18 shows a schematic of a system for the soft ablative desorption and mass analysis of a sample.

FIG. 18 shows an example of a laser system combined with a mass spectrometer which may be used according to embodiments of the present invention. An amplified femtosecond laser system is used to generate broad band laser pulses spanning the UV to visible, as well as the pulses for soft ablative desorption. The laser system for this application, as shown, is based on the work of D. Kraemer, M. Cowan, R. Hua, K. Franjic, and R. J. D. Miller, "High Power Femtosecond Infrared Laser Source Based on Noncollinear Optical Parametric Chirped Pulse Amplification", *J. Opt. Soc. Am. B* 2007, 24(4), 813-818.

The tunable IR and UV to visible pulses are generated using optical parametric amplifiers. The IR pulses are generated by an optical parametric amplifier 950 that is pumped by a 1.06 micron amplifier 952 and the amplified output of a 1.55 micron Er fiber laser 952. Output from the Er laser is split into two amplifying fibers 956, each followed by a nonlinear fiber 958. One path provides a seed for the amplifier 952, and the other provides a signal seed for parametric amplifier 950. The idler output from the parametric amplifier 950 is reflected by beamsplitter 960 and provides the optical beam 962 for soft ablative desorption. This beam is directed onto a sample under ambient conditions near the inlet 962 of mass spectrometer 964. With respect to photoionization, the UV to Vis pulses generated from the signal output beam 968 of the parametric amplifier 950 in vacuum chamber 970 housing a hollow fiber 972 filled with Ar gas. The output is spectrally filtered with filter 974 to match the electronic spectrum of the molecule of interest with respect to ionizing for mass spectroscopic detection.

Figure 17:
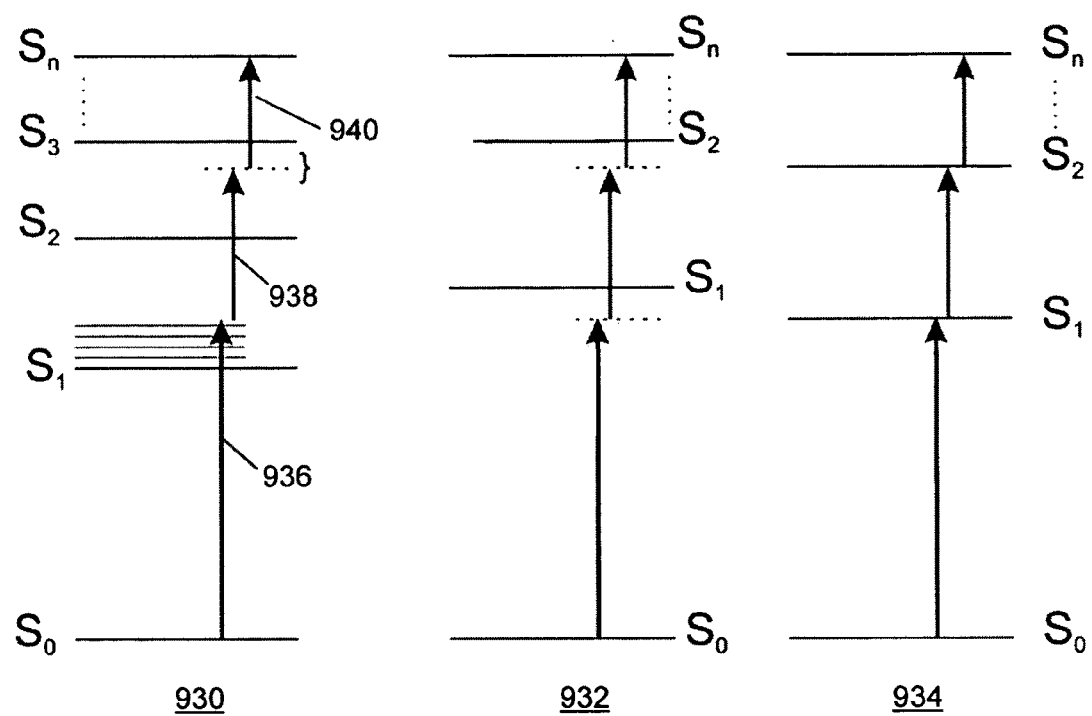
FIG. 17 shows non-resonant and resonant linear photo-ionization for the selective ionization of a specific molecule (the optical chromatography process).

The resonantly matched pulses have pulse durations of less than 1 picosecond, the time for nonradiative relaxation of the electronic levels that destroys the resonant ladder climbing process depicted in FIGS. 16 and 17. For VUV pulses, the peak power is sufficient with conventional femtosecond lasers to use high harmonic generation using gas cells to attain the necessary wavelengths and energies for saturated, 100%, ionization of the molecules of interest as part of the mass spectrometry detection. The timing between all the pulses can be handled by simply varying the pathlengths between the beams to be multiplexed using fibre optics of varying lengths optimized for the process. Furthermore, in the timing between the injection of an ionized plume into the mass analysis device and the subsequent mass analysis step can be coordinated by providing a signal obtained from a power measurement of one of the optical beams. In one non-limiting example, a signal is obtained by measuring a portion of the time-dependent optical power transmitted through a beamsplitter or dichroic mirror, and this signal is provided (optionally after conditioning the signal with a control circuit) as an external signal or trigger to the mass spectrometer, preferably with a corresponding phase or delay input that may be manually set through a calibration procedure.

Thus, the ionization step is achieved through the use of timed VUV pulse generated through high harmonic generation (using for example the same laser used to generate the IR), as shown in FIG. 18. The wavelength of the VUV is tuned to provide the minimum energy to remove an electron and create a parent ion for mass spec identification. This feature is important to minimize the fragmentation pattern to assist in identification of the molecule; although it is recognized that tuning the VUV wavelength above this threshold can be exploited to change the fragmentation pattern in known ways, intrinsic to the molecule, to further assist in identification of the molecular species.

As discussed above, the soft ablative desorption mechanism is effective in generating a well timed plume of gas phase molecules in its native state, with a small angular divergence. There is no steady state or continuous wave source VUV radiation with sufficient flux or number photons/unit area, to significantly photoionize the sample and fully achieve the sensitivity limits of mass spectrometry. The level of focused VUV radiation requires a focused laser beam in this wavelength regime to achieve sufficient flux to excite and photoionize nearly all molecules within the generated ablation plume. Such sources of VUV radiation, with sufficient pulse energies or VUV photons, are currently only available with short pulsed lasers of less than 100 ns duration.

The well synchronized pulse of gas phase molecules achieved through soft ablative desorption as shown schematically in the figures enables the tight focusing conditions of VUV laser sources for maximum photoionization, as shown schematically in FIG. 12. As noted above, this same ionization step can be performed with a series of well timed visible to UV, 1-photon resonances that match the electronic spectrum of the molecule of interest for higher efficiency with respect to laser conversion of the necessary light and to provide additional contrast against background molecular species. This last step of photogeneration of ions by either a single VUV pulse or a sequence of visible to UV resonantly matched pulses, in combination with soft ablative desorption of gas phase analyte, produces parent ions with the small amounts of excess energy.

This process depends explicitly on the unique molecular absorption cross sections for the absorption of light at these wavelengths. The process of ion generation by this step depends solely on the absorption cross section in the case of VUV photoionization and is highly reproducible. Similarly, for UV/Vis excitation the absorption depends on the product of the absorption cross sections and is again reproducible for a given pulse energy/spectrum. Thus, this approach solves the problem of irreproducible ionization and improves the quantitative power of mass spectrometry for clinical applications. Furthermore, this invention solves the problem of molecular fragmentation. These two features potentially enable mass spectrometry to achieve near single molecule detection limits. Attaining this limit is important as there is no background congestion to complicate assignments of mass peaks to molecular species. Accordingly, aspects of this invention enable the extension of mass spectroscopic methods to the characterization of biomarkers without prior purification.

For additional contrast in species identification, it may be desirable to have fragmentation, although such fragmentation must also be deterministic as in the photogeneration of ions. By controlling the colours or spectral component of the VUV and Vis to UV in the pulse composition, it is possible to obtain specific fragmentation as desired by coupling the light to specific molecular vibronic levels, to provide energy above the minimum for ionization (threshold ionization) and thereby give well defined fragmentation patterns as needed to identify molecules.

Embodiments of the present invention may be applied to direct determination of molecular composition of biological materials. Aspects of the invention make it possible to take a single drop of blood from a patient and provide molecular level diagnosis of wellness and the early detection of disease markers.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A method of performing the soft desorption of analyte from a sample, said method comprising the steps of:
   irradiating said sample with an optical beam; and
   optically exciting vibrational levels of a component of said sample within an irradiated zone;
   wherein said sample is irradiated for a time interval that is less than a time duration required for energy loss beyond said irradiated zone to thermal diffusion and acoustic expansion; and wherein energy absorbed from said optical beam by said component is sufficient to superheat said component and cause the ejection of an ablation plume from said irradiated zone.

2. The method according to claim 1 wherein said ablation plume comprises said analyte in a gas phase.

3. The method according to claim 1 wherein said analyte desorbed from said sample is desorbed in an unexcited state.

4. The method according to claim 1 wherein analyte desorbed from said sample is desorbed in a neutral state.

5. The method according to claim 1 wherein a concentration of said component is such that said irradiated zone has a depth on a micron scale.

6. The method according to claim 1 wherein said component is water.

7. The method according to claim 6 wherein said optical beam excites one of OH stretching vibrations, OH bend modes, and a combination thereof.

8. The method according to claim 6 wherein an energy flux of said optical beam at said sample is at least 0.1 J/cm$^2$.

9. The method according to claim 6 wherein said time interval is between approximately 100 fs and 1 ns.

10. The method according to claim 9 wherein said time interval is less than 100 ps.

11. The method according to claim 1 wherein a transverse spatial profile of said optical beam is substantially uniform in intensity.

12. The method according to claim 1 wherein said optical beam comprises a laser pulse.

13. The method according to claim 1 wherein an intensity of said optical beam is less than a threshold for multi-photon absorption.

14. The method according to claim 1 wherein said sample comprises a biological sample.

15. The method according to claim 14 wherein said sample is selected from the list comprising tissue, cells, organs, bodily fluids, urine, blood, serum, plasma, cerebral spinal fluid, and sputum.

16. The method according to claim 1 wherein a thickness of said sample is approximately equal to an absorption depth of said optical beam.

17. The method according to claim 16 wherein said sample is provided on a substrate, wherein said substrate is transparent to said optical beam, said method comprising the step of irradiating said sample through a back surface of said substrate.

18. The method according to claim 16 wherein said sample is a liquid sample, and said liquid sample is provided in a microwell.

19. The method according to claim 18 wherein said microwell is formed in a substrate, wherein said substrate is transparent to said optical beam, said method comprising the step of irradiating said sample through a back surface of said substrate.

20. The method according to claim 19 wherein said substrate comprises a material selected from the list comprising silicon, sapphire and $SiO_2$.

21. The method according to claim 1 further comprising the step of providing an array of samples on a sample holder, and wherein said steps of performing soft desorption of analyte from a sample is repeated for each sample within said array of samples.

22. The method according to claim 21 wherein said array of samples comprises an array of liquid samples, each said sample contained within a well.

23. The method according to claim 22, further comprising the step of filling said wells by a capillary prior to said step of irradiating said sample.

24. The method according to claim 23 wherein said capillary is a component of a separation system employed to separate analyte within said sample prior to said step of irradiating said sample.

25. The method according to claim 24 wherein a position of a well filled from said capillary is correlated with a dispensing sequence.

26. The method according to claim 23 wherein said capillary is employed as a sampling device prior to dispensing said sample into said wells.

27. The method according to claim 21 wherein said sample holder is housed said housing comprising:
a support platform for receiving said sample holder;
a reservoir for maintaining a vapor pressure within said housing;
a slidable cover removably attached to said support platform for enclosing said sample holder and said reservoir within said housing, said cover further comprising an aperture for providing external access for said optical beam to at least one well when said sample holder is enclosed within said housing, and wherein said cover may translated to positioned said aperture over each of said one or more wells while enclosing a remainder of said one or more wells and said reservoir;
said method further comprising the steps of:
placing said sample holder onto said support platform;
filling said reservoir with a liquid selected to stabilize a meniscus within said wells when said wells are filled;
enclosing said sample holder and said reservoir with said cover; and
translating said cover to position said aperture over said given well when performing said steps of soft desorption of analyte.

28. The method according to claim 1 wherein said optical beam is a second optical beam, and wherein analyte resides within said sample in a complex, said method further comprising the steps of:
prior to said step of irradiating said sample with said second optical beam, irradiating said sample with a first optical beam;
wherein said first optical beam has a frequency selected to cause dissociation of said complex.

29. The method according to claim 28 wherein said complex is a protein complex bound by an amide bond, and wherein a wavelength of said first beam is approximately 1600 cm$^{-1}$ for the breaking of said amide bond.

30. The method according to claim 16 wherein said optical beam is a first optical beam, said method further comprising the steps of:
positioning a substrate comprising a well above said sample prior to irradiating said sample with said first optical beam, said well having a liquid contained therein, wherein said well is positioned to receive at least a portion of said ablation plume within said liquid;
receiving said ablation plume within said liquid;
irradiating said liquid with a second optical beam; and
optically exciting vibrational levels of a component of said liquid within an irradiated zone of said liquid;
wherein said liquid is irradiated for a time interval that is less than a time duration required for energy loss beyond said irradiated zone to thermal diffusion and acoustic expansion; and
wherein energy absorbed from said second optical beam by said component of said liquid is sufficient to superheat said component of said liquid and cause the ejection of an ablation plume from said irradiated zone of said liquid.

31. The method according to claim 30 wherein said liquid comprises an agent for releasing said analyte from a complex.

32. The method according to claim 31 wherein said agent comprises a denaturing agent.

33. The method according to claim 31 wherein said sample comprises a heterogeneous sample, wherein said analyte is initially bound in a complex, and wherein said agent dissociates said complex prior to said step of irradiating said liquid with said second optical beam.

34. The method according to claim 30, wherein said substrate comprises an array of wells, each said well having a liquid contained therein, wherein two or more of said wells receive a portion of said ablation plume for providing spatially resolved desorption of said sample, and wherein said steps of irradiating said liquid with a second optical beam and optically exciting vibrational levels of a component of said liquid within an irradiated zone of said liquid are serially performed for each of said two or more wells on a single-well basis.

35. The method according to claim 34 wherein said liquid comprises an agent for releasing said analyte from a complex.

36. The method according to claim 35 wherein said agent comprises a denaturing agent.

37. The method according to claim 35 wherein said sample comprises a heterogeneous sample, wherein said analyte is initially bound in a complex, and wherein said agent dissociates said complex prior to said step of irradiating said liquid with said second optical beam.

38. The method according to claim 34 wherein said each well in said array of wells comprises a diameter on the micron scale for spatially resolving analyte desorbed from said sample.

39. The method according to claim 34 wherein said each well in said array of wells comprises a diameter on the submicron scale for spatially resolving analyte desorbed from said sample, and wherein said substrate is transparent to said second optical beam, and wherein said second optical beam is delivered by a near-field optical element.

40. The method according to claim 1 further comprising the step of analyzing said desorbed analyte with an analytic device.

41. The method according to claim 40 wherein said analytic device is a mass analyzer, and wherein said method further comprises the step of ionizing said desorbed analyte prior to said step of analyzing said desorbed analyte.

42. The method according to claim 41 wherein said mass analyzer is selected from the list comprising a sector mass spectrometer, a time-of-flight mass spectrometer, an ion-trap mass spectrometer, a quadrupole mass spectrometer, and combinations thereof.

43. The method according to claim 41 wherein said step of ionizing said desorbed analyte is achieved using an ionization method selected from the list comprising coronal discharge ionization, electrospray ionization, chemical ionization, and thermal emission ionization.

44. The method according to claim 41, said method further comprising the steps of positioning said sample so that said ablated plume is directed into the inlet of a mass spectrometer for subsequent mass analysis.

45. The method according to claim 44 wherein a spacing between said sample and said inlet is approximately 100 microns, and wherein a pressure in the region between said sample and said inlet maintained at a prescribed level by differential pumping.

46. The method according to claim 45 wherein said pressure is maintained at approximately 5 Torr.

47. The method according to claim 41 wherein said desorbed analyte is photo-ionized within an evacuated region prior to mass analysis, said method further comprising the steps of:
positioning said sample so that said ablated plume passes through an aperture into said evacuated region;
irradiating said ablation plume within said evacuated region with a vacuum-ultraviolet beam having a wavelength selected to photo-ionize said desorbed analyte; and
performing mass analysis of said ionized analyte.

48. The method according to claim 47 wherein a spacing between said sample and said aperture is approximately 100 microns, and wherein a pressure in the region between said sample and said inlet maintained at a prescribed level by differential pumping.

49. The method according to claim 48 wherein said pressure is maintained at approximately 5 Torr.

50. The method according to claim 47 wherein said aperture is an inlet to said mass spectrometer, and said evacuated region is within said mass spectrometer.

51. The method according to claim 47 wherein said sample is optically thick and recoil material is ejected after said ablation plume, said method comprising the step of irradiating only said ablation plume, so that said recoil material is not ionized.

52. The method according to claim 47 wherein an interaction length between said vacuum ultraviolet beam and said ablation plume is extended using an optical cavity formed within said evacuated region.

53. The method according to claim 44 wherein said desorbed analyte is photo-ionized prior to mass analysis through a linear resonant process, said method further comprising the steps of:
irradiating said ablation plume with a photo-ionizing beam, wherein said photo-ionizing beam comprises a frequency spectrum and a phase profile for the resonant linear photo-ionization of said desorbed analyte; and
performing mass analysis of said ionized analyte.

54. The method according to claim 53 wherein said ablation plume is photo-ionized by said photo-ionizing beam prior to entering said inlet.

55. The method according to claim 53 wherein said frequency spectrum comprises spectral components for producing one-photon linear absorption between adjacent levels to ionize said analyte and a phase profile selected to provide the sequential one-photon excitation between said levels from a first level to an ionized state.

56. The method according to claim 55 wherein said ablation plume comprises a plurality of molecular species, and wherein said analyte is selectively ionized.

57. The method according to claim 55 wherein a spacing between said sample and said inlet is approximately 100 microns, and wherein a pressure in the region between said sample and said inlet maintained at a prescribed level by differential pumping.

58. The method according to claim 57 wherein said pressure is maintained at approximately 5 Torr.

59. The method according to claim 44 wherein said desorbed analyte is photo-ionized prior to mass analysis through a two-photon resonant process, said method further comprising the steps of:
irradiating said ablation plume with a photo-ionizing beam, wherein said photo-ionizing beam comprise a frequency spectrum for exciting said analyte to a first excited state by two photon absorption, driving said excited state into saturation, and ionizing said excited analyte in a linear regime; and performing mass analysis of said ionized analyte.

60. A method of preparing a sample for mass analysis, said method comprising the steps of:
   irradiating a sample with an optical beam; and
   optically exciting vibrational levels of a component of said sample within an irradiated zone;
   wherein said sample is irradiated for a time interval that is less than a time duration required for energy loss beyond said irradiated zone to thermal diffusion and acoustic expansion;
   wherein energy absorbed from said optical beam by said component is sufficient to superheat said component and cause the ejection of an ablation plume from said irradiated zone;
   ionizing said ablation plume with an ionizing means; and
   directing said ionized ablation plume into an inlet of a mass analysis device.

61. A method of performing mass analysis on a sample, said method comprising the steps of:
   irradiating said sample with an optical beam; and
   optically exciting vibrational levels of a component of said sample within an irradiated zone;
   wherein said sample is irradiated for a time interval that is less than a time duration required for energy loss beyond said irradiated zone to thermal diffusion and acoustic expansion;
   wherein energy absorbed from said optical beam by said component is sufficient to superheat said component and cause the ejection of an ablation plume from said irradiated zone;
   ionizing said ablation plume with an ionizing means;
   directing said ionized ablation plume into an inlet of a mass analysis device; and
   performing mass analysis on said ionized ablation plume.

62. A system for desorbing an analyte, wherein said sample comprises a component having an excitation spectrum comprising vibrational energy levels, said system comprising:
   an optical apparatus for directing an optical beam onto a sample and irradiating an irradiation volume within said sample, said optical beam comprising:
   a frequency spectrum for optically exciting vibrational levels of a component of said sample;
   a time duration shorter that is less than a timescale required for energy loss beyond said irradiated zone to thermal diffusion and acoustic expansion; and
   sufficient energy to superheat said component and cause ejection of an ablation plume from said irradiated zone.

63. The system according to claim 62 wherein said component is water and wherein an energy flux of said optical beam at said sample is at least 0.1 J/cm$^2$.

64. The system according to claim 62 wherein said time duration is between approximately 100 fs and 1 ns.

65. The system according to claim 64 wherein said time interval is less than 100 ps.

66. The system according to claim 62 wherein a transverse spatial profile of said optical beam is substantially uniform in intensity.

67. The system according to claim 62 wherein said optical source apparatus comprises a laser and said optical beam comprises a laser pulse.

68. The system according to claim 62 wherein an intensity of said optical beam is less than a threshold for multi-photon absorption.

69. The system according to claim 62 wherein an absorption depth of said optical beam is approximately equal to a thickness of said sample.

70. The system according to claim 62 further comprising a substrate for supporting said sample, wherein said substrate is transparent to said optical beam, wherein said beam is directed through a back surface of said substrate onto said sample.

71. The system according to claim 62 wherein said sample is provided in a microwell formed in a substrate, wherein said substrate is transparent to said optical beam, wherein said beam is directed through a back surface of said substrate.

72. The system according to claim 62 further comprising an array of microwells supported on a sample holder and a capillary apparatus for filling said microwells with a plurality of samples.

73. The system according to claim 62 further comprising:
   an ionization means for ionizing said ablation plume; and
   a mass spectrometer for performing mass analysis on said desorbed analyte;
   wherein said sample is positioned to direct said ablation plume through an inlet of said mass spectrometer.

74. The system according to claim 73 wherein ionization means is selected from the list comprising a coronal discharge ionization apparatus, electrospray ionization apparatus, chemical ionization apparatus, and thermal emission ionization apparatus.

75. The system according to claim 73 wherein a spacing between said sample and said inlet is approximately 100 microns, and wherein a pressure in the region between said sample and said inlet maintained at a prescribed level by differential pumping.

76. The system according to claim 73 wherein said ionization means comprises a second optical apparatus for directing a vacuum-ultraviolet beam onto said ablation plume within an evacuated region, wherein said vacuum-ultraviolet beam photo-ionizes said desorbed analyte.

77. The system according to claim 76 wherein said evacuated region comprises an optical cavity for increasing an interaction length between said vacuum ultraviolet beam and said ablation plume.

78. The system according to claim 73 wherein said ionization comprises a second optical apparatus for directing a photo-ionizing beam onto said ablation plume, wherein said photo-ionizing beam comprises a frequency spectrum and a phase profile for the resonant linear photo-ionization of said desorbed analyte.

79. The system according to claim 78 wherein said photo-ionizing beam is directed onto said ablation plume on an external side of said inlet.

80. The system according to claim 78 wherein said frequency spectrum comprises spectral components for producing one-photon linear absorption between adjacent levels to ionize said analyte and a phase profile selected to provide the sequential one-photon excitation between said levels from a first level to an ionized state.

* * * * *